(12) United States Patent
Watanabe et al.

(10) Patent No.: US 6,949,566 B2
(45) Date of Patent: Sep. 27, 2005

(54) THIAZOLE AND OXAZOLE DERIVATIVES

(75) Inventors: Fumihiko Watanabe, Osaka (JP); Yoshinori Tamura, Osaka (JP)

(73) Assignee: Shionogi & Co. Ltd., Osaka (JP)

( * ) Notice: Subject to any disclaimer, the term of this patent is extended or adjusted under 35 U.S.C. 154(b) by 0 days.

(21) Appl. No.: 10/381,280

(22) PCT Filed: Sep. 28, 2001

(86) PCT No.: PCT/JP01/08507

§ 371 (c)(1), (2), (4) Date: Mar. 24, 2003

(87) PCT Pub. No.: WO02/28844

PCT Pub. Date: Apr. 11, 2002

(65) Prior Publication Data

US 2004/0024029 A1 Feb. 5, 2004

(30) Foreign Application Priority Data

Sep. 29, 2000 (JP) .......... 2000-298199

(51) Int. Cl.[7] .......... A61K 31/423; A61K 31/428; C07D 263/57; C07D 277/66; C07D 413/12
(52) U.S. Cl. .......... 514/307; 514/311; 514/340; 514/365; 514/374; 546/144; 546/167; 546/270.4; 546/271.4; 548/204; 548/236
(58) Field of Search .......... 546/144, 167, 546/271.4, 270.4; 548/204, 236; 514/307, 311, 340, 365, 374

(56) References Cited

U.S. PATENT DOCUMENTS 6,423,729 B1 * 7/2002 Kurihara et al. .......... 514/364

FOREIGN PATENT DOCUMENTS

| EP | 757037 A2 | 2/1997 |
| EP | 0950656 A1 | 10/1999 |
| EP | 1029541 A1 | 8/2000 |
| WO | WO 99/04780 A1 | 2/1999 |

OTHER PUBLICATIONS

Ho et al., "Gene Expression, Purification and Characterization of Recombinant Human Neutrophil Collagenase," Gene, vol. 146, pp. 297–301 (1994).

Okada et al., "Matrix Metalloproteinase 9 (92–kDa Gelatinase/Type IV Collagenase) from HT 1080 Human Fibrosarcoma Cells," The Journal of Biological Chemistry, vol. 267, No. 30, pp. 21712–21719 (1992).

Okada et al., "Matrix Metalloproteinase 2 from Human Rheumatoid Synovial Fibroblasts," Eur. J. Biochem., vol. 194, pp. 721–730 (1990).

Ward et al., "The Purification of Tissue Inhibitor of Metalloproteinases–2 from Its 72 kDa Progelatinase Complex," Biochem J., vol. 278, pp. 179–187 (1991).

Knight et al., "A Novel Coumarin–labelled Peptide for Sensitive Continuous Assays of the Matrix Metalloproteinases," vol. 296, No. 3, pp. 263–266 (1992).

* cited by examiner

Primary Examiner—Fiona T. Powers
(74) Attorney, Agent, or Firm—Foley & Lardner LLP

(57) ABSTRACT

A compound of the formula (I):

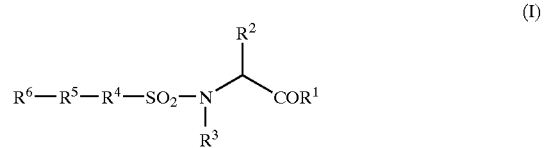

(I)

wherein $R^1$ is hydroxy and the like; $R^2$ is optionally substituted lower alkyl and the like; $R^3$ is hydrogen atom and the like; $R^4$ is optionally substituted arylene and the like;

$R^5$ is a group represented by the formula:

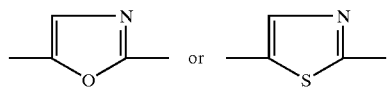

and the like; $R^6$ is optionally substituted aryl and the like, its optically active substance, its prodrug, their pharmaceutically acceptable salt, or solvate thereof and metalloproteinase inhibitors containing them.

16 Claims, No Drawings

THIAZOLE AND OXAZOLE DERIVATIVES

TECHNICAL FIELD

This invention relates to thiazole and oxazole derivatives and metalloproteinase inhibitors containing them.

BACKGROUND ART

An extracellular matrix, consisting of collagen, fibronectin, laminin, proteoglycan, etc., has a function to support tissues, and plays a role in propagation, differentiation, adhesion, or the like in cells. Metalloproteinases which are protease having a metal ion in the active center, especially matrix metalloproteinases (MMP), are concerned with the degradation of the extracellular matrix. Many types of MMP, from MMP-1 (collagenase type I) to MMP-23, have been reported as enzymes working for the growth, remodeling of tissues, etc. under usual physiological conditions. It is reported, however, that the progression of various kinds of diseases involving breakdown and fibrosis of tissues (e.g., osteoarthritis, rheumatoid arthritis, corneal ulceration, periodontitis, metastasis and invasion of tumor, and virus infection (HIV infection)) is related with increase of the manifestation or activity of the above-mentioned enzyme.

Sulfonamide derivatives containing a oxazole group are disclosed in WO 99/04780 and the like.

Sulfonamide derivatives having an inhibitory activity against MMP are disclosed in WO 97/27174 and WO 99/4780 and the like.

DISCLOSURE OF INVENTION

The inhibition of such MMP activities is considered to contribute to the improvement and prevention of the above-mentioned diseases caused by or related to the activity. Therefore, the development of MMP inhibitors has been desired.

In the above situation, inventors of the present invention have found that certain sulfonamide derivatives having an oxadiazole or thiazole ring have a potent inhibitory activity against several MMPs.

Inventors of the present invention have accomplished the present invention.

The present invention relates to: I) A compound of the formula (I):

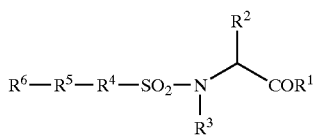

wherein $R^1$ is NHOH, hydroxy, or lower alkyloxy;
$R^2$ is hydrogen atom, optionally substituted lower alkyl, optionally substituted aryl, optionally substituted aralkyl, optionally substituted heteroaryl, or optionally substituted heteroarylalkyl;
$R^3$ is hydrogen atom, optionally substituted lower alkyl, optionally substituted aryl, optionally substituted aralkyl, optionally substituted heteroaryl, or optionally substituted heteroarylalkyl;
$R^4$ is optionally substituted arylene, or optionally substituted heteroarylene;
$R^5$ is a group represented by the formula:

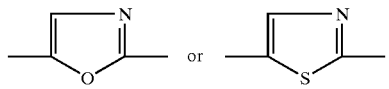

$R^6$ is optionally substituted aryl, optionally substituted heteroaryl or optionally substituted non-aromatic heterocyclic group; provided that $R^5$ is thiazole-2,5-diyl when $R^4$ is thiophene-2,5-diyl and $R^6$ is optionally substituted phenyl, its optically active substance, its prodrug, their pharmaceutically acceptable salt, or solvate thereof.

In more detail, the invention relates to the following II)–XVI).
II) A compound described in I), wherein $R^6$ is a group represented by the formula:

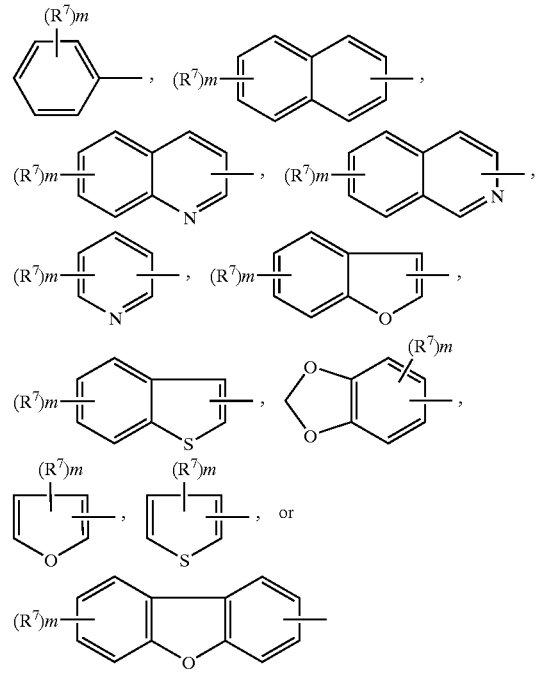

wherein $R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, or optionally substituted amino;
m is 0, 1, 2, or 3,
its optically active substance, its prodrug, their pharmaceutically acceptable salt, or solvate thereof.
III) A compound, its optically active substance, its prodrug, their pharmaceutically acceptable salt, or solvate thereof described in I) or II), wherein $R^1$ is hydroxy.
IV) A compound, its optically active substance, its prodrug, their pharmaceutically acceptable salt, or solvate thereof as described in any one of I) to III), wherein $R^2$ is lower alkyl optionally substituted with carboxy, carbamoyl or lower alkylthio, aryl optionally substituted with hydroxy, aralkyl optionally substituted with hydroxy, or heteroarylalkyl optionally substituted with hydroxy, or hydrogen.
V) A compound, its optically active substance, its prodrug, their pharmaceutically acceptable salt, or solvate thereof as described in any one of I) to IV), wherein $R^2$ is hydrogen atom, methyl, isopropyl, isobutyl, benzyl, indol-3-ylmethyl, carboxymethyl, carboxyethyl, 2-methylthioethyl, 4-hydroxy-benzyl, or (5-hydroxy-indol-3-yl)methyl.

VI) A compound, its optically active substance, its prodrug, their pharmaceutically acceptable salt, or solvate thereof as described in any one of I) to V), wherein $R^3$ is hydrogen atom.

VII) A compound, its optically active substance, its prodrug, their pharmaceutically acceptable salt, or solvate thereof as described in any one of I) to VI), wherein $R^4$ is 1,4-phenylene or 2,5-thiophene-diyl.

VIII) A compound, its optically active substance, as described in any one of I) to VII), wherein $R^6$ is a group represented by the formula:

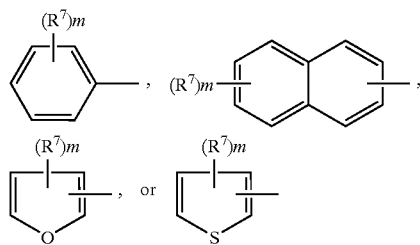

wherein $R^7$ and m are as defined above.

its prodrug, their pharmaceutically acceptable salt, or solvate thereof.

IX) A compound, as described in any one of I) to VIII), wherein $R^6$ is a group represented by the formula:

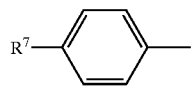

wherein $R^7$ is as defined above, its optically active substance, its prodrug, their pharmaceutically acceptable salt, or solvate thereof.

X) A compound of the formula (II):

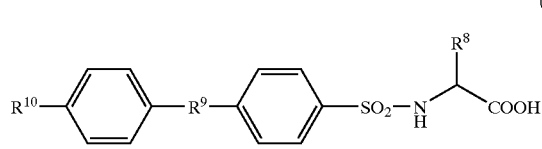

(II)

wherein $R^8$ is hydrogen atom, methyl, isopropyl, isobutyl, carboxymethyl, carboxyethyl, 2-methylthioethyl, benzyl, 4-hydroxybenzyl, or indol-3-ylmethyl;

$R^9$ is a group represented by the formula:

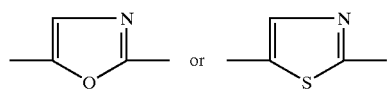

$R^{10}$ is hydrogen atom, halogen, lower alkyl, lower alkyloxy, halo(lower)alkyl, acyl, nitro, cyano, optionally substituted amino, or hydroxy, its optically active substance, its prodrug, their pharmaceutically acceptable salt, or solvate thereof.

XI) A compound of the formula (III):

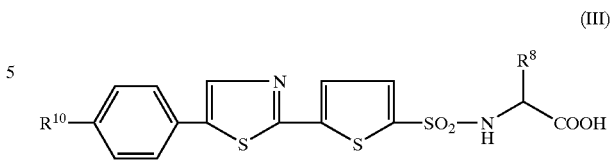

(III)

wherein $R^8$ is hydrogen atom, methyl, isopropyl, isobutyl, carboxymethyl, carboxyethyl, 2-methylthioethyl, benzyl, 4-hydroxybenzyl, or indol-3-ylmethyl;

$R^{10}$ is hydrogen atom, halogen, lower alkyl, lower alkyloxy, halo(lower)alkyl, acyl, nitro, cyano, optionally substituted amino, or hydroxy, its optically active substance, its prodrug, their pharmaceutically acceptable salt, or solvate thereof.

XII) A pharmaceutical composition containing a compound of any one of I) to XI) as an active ingredient.

XIII) A composition for inhibiting metalloproteinase containing a compound of any one of I) to XI) as an active ingredient.

XIV) A composition for inhibiting matrix metalloproteinase containing a compound of any one of I) to XI) as an active ingredient.

XV) Use of a compound of any one of I) to XI) for preparation of a pharmaceutical composition for treating diseases caused by or related to metalloproteinase.

XVI) A method for treating a mammal, including a human, to alleviate the pathological effects of diseases caused by or related to metalloproteinase, which comprises administration to said mammal of a compound as described in any one of I) to XI) in a therapeutically effective amount.

XVII) A composition for treating or preventing cancer, containing a compound of any one of I) to XI) as an active ingredient.

XVIII) A composition for treating or preventing nephritis, containing a compound of any one of I) to XI) as an active ingredient.

XIX) A composition for treating or preventing osteoarthritis, containing a compound of any one of I) to XI) as an active ingredient.

XX) A composition for treating or preventing heart failure, containing a compound of any one of I) to XI) as an active ingredient.

XXI) A composition for treating or preventing rheumatoid arthritis, containing a compound of any one of I) to XI) as an active ingredient.

XXI) A composition for treating or preventing chronic obstructive pulmonary disease, containing a compound of any one of I) to XI) as an active ingredient.

In the present specification, the term "lower alkyl" employed alone or in combination with other terms means a straight- or branched chain monovalent hydrocarbon group having 1 to 8 carbon atom(s). Examples of the alkyl include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like. $C_1$ to $C_6$ alkyl is preferred. $C_1$ to $C_3$ alkyl is more preferred.

In the present specification, the term "lower alkenyl" employed alone or in combination with other terms means a straight- or branched chain monovalent hydrocarbon group having 2 to 8 carbon atoms and at least one double bond. Examples of the alkenyl include vinyl, allyl, propenyl, crotonyl, isopentenyl, a variety of butenyl isomers and the like. $C_2$ to $C_6$ alkenyl is preferred. $C_2$ to $C_4$ alkenyl is more preferred.

The term "lower alkynyl" used in the present specification means a straight- or branched chain monovalent hydrocarbon group having 2 to 8 carbon atoms and at least one triple bond. The alkynyl may contain (a) double bond(s). Examples of the alkynyl include ethynyl, 2-propynyl, 3-butynyl, 4-pentynyl, 5-hexynyl, 6-heptynyl, 7-octynyl and the like. $C_2$ to $C_6$ alkynyl is preferred. $C_2$ to $C_4$ alkynyl is more preferred.

The term "cycloalkyl" used in the present specification includes cycloalkyl group having 3 to 8 carbon atoms. Examples of cycloalkyl group include cyclopropyl, cyclobutyl, cyclopentyl, cyclohexyl, cycloheptyl, cyclooctyl and the like. $C_3$ to $C_6$ cycloalkyl is preferred.

In the present specification, the term "aryl" employed alone or in combination with other terms includes monocyclic or condensed ring aromatic hydrocarbons. Examples of the aryl include phenyl, 1-naphtyl, 2-naphtyl, anthryl, and the like.

Preferable is phenyl as "aryl" for $R^2$.

Preferable is phenyl as "aryl" for $R^3$.

Preferable is phenyl, 1-naphtyl and 2-naphtyl as "aryl" for $R^6$.

The term "aralkyl" herein used means the above-mentioned "lower alkyl" substituted with one or more above-mentioned "aryl" at any possible position. Examples of the aralkyl are benzyl, phenylethyl (e.g., 2-phenethyl and the like), phenylpropyl (e.g., 3-phenylpropyl and the like), naphthylmethyl (e.g., 1-naphthylmethyl and 2-naphthylmethyl and the like), anthrylmethyl (e.g., 9-anthrylmethyl and the like), and the like. Benzyl and phenylethyl are preferred.

In the present specification, the term "heteroaryl" employed alone or in combination with other terms includes a 5 to 6 membered aromatic heterocyclic group which contains one or more hetero atoms selected from the group consisting of oxygen, sulfur, and nitrogen atoms in the ring and may be fused with cycloalkyl, aryl, non-aromatic heterocyclic group, and other heteroaryl at any possible position. Examples of the heteroaryl are pyrrolyl (e.g., 1-pyrrolyl, 2-pyrrolyl, 3-pyrrolyl), furyl (e.g., 2-furyl, 3-furyl), thienyl (e.g., 2-thienyl 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolyl (2-isoindolyl), indolyl (e.g., 1-indolyl, 2-indolyl, 3-indolyl), indazolyl (e.g., 3-indazolyl), puriyl (e.g., 8-puriyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinoxanyl (2-quinoxanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 3-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzimidazolyl (e.g., 2-benzimidazolyl), benzisoxazolyl (e.g., 3-benzisoxazolyl), benzoxazolyl (e.g., 2-benzoxazolyl), benzoxadiazolyl (e.g., 4-benzoxadiazolyl), benzisothiazolyl (e.g., 3-benzisothiazolyl), benzothiazolyl (e.g., 2-benzothiazolyl), benzofuryl (e.g., 3-benzofuryl), benzothienyl (e.g., 2-benzothienyl), benzodioxolanyl (e.g., 5-benzodioxolanyl) and the like.

Preferable are indolyl, imidazolyl and the like as "heteroaryl" for $R^2$.

Preferable are pyridyl, thienyl, furyl, imidazolyl and the like as "heteroaryl" for $R^3$.

Preferable are quinolyl (e.g., 2-quinolyl), pyridyl (e.g., 3-pyridyl), benzofuranyl (e.g., 2-benzofuranyl), benzothienyl (e.g., 2-benzothienyl), dibenzofuranyl, isoquinolyl (e.g., 3-isoquinolyl), thienyl (e.g., 2-thienyl), furyl (e.g., 2-furyl), benzodioxolanyl and the like as "heteroaryl" for $R^6$.

The term "heteroarylalkyl" herein used includes the above mentioned "lower alkyl" substituted with at least one above-mentioned "heteroaryl" at any possible position. Examples of the heteroarylalkyl are thiazolylmethyl (e.g., 4-thiazolylmethyl), thiazolylethyl (e.g., 5-thiazolyl-2-ethyl), benzothiazolylmethyl (e.g., benzothiazol-2-ylmethyl), indolylmethyl (e.g., indol-3-ylmethyl), imidazolylmethyl (e.g., 4-imidazolylmethyl), benzothiazolylmethyl (e.g., 2-benzothiazolylmethyl), indazolylmethyl (e.g., 1-indazolylmethyl), benzotriazolylmethyl (e.g., 1-benzotriazolylmethyl), benzoquinolylmethyl (e.g., 2-benzoquinolylmethyl), benzimidazolylmethyl (e.g., 2-benzimidazolylmethyl), pyridylmethyl (e.g., 4-pyridylmethyl), and the like.

Examples as "heteroarylalkyl" for $R^2$ are indolylmethyl (e.g., indol-3-ylmethyl) and imidazolylmethyl (imidazol-5-ylmethyl) and the like.

In the present specification, the term "non-aromatic heterocyclic group" employed alone or in combination with other terms includes a 5 to 7 membered non-aromatic ring which contains one or more hetero atoms selected from the group consisting of oxygen, sulfur, and nitrogen atoms in the ring and a condensed ring which are formed with two or more of the non-aromatic ring. Examples of the non-aromatic heterocyclic group are pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidinyl (piperidino, 2-piperidinyl), piperazinyl (e.g., 1-piperazinyl), indolynyl (e.g., 1-indolynyl), isoindolinyl (e.g., isoindolinyl), morpholinyl (e.g., morpholino, 3-morpholinyl), 4H- [1,2,4]oxaziazole-5-one, 1,2,3,4-tetrahydro-[1,8]naphtylidine, 1,3-benzodioxolyl and the like.

Preferable are pyrazolidinyl, piperidyl, pyrrolinyl, morpholinyl, 1,3-benzodioxolyl and the like as "non-aromatic heterocyclic group" for $R^6$.

The term "arylene" herein used means a divalent group of the above-mentioned "aryl". Examples of the arylene are phenylene, naphthylene, and the like. Mentioned in more detail, it is exemplified by 1,2-phenylene, 1,3-phenylen, 1,4-phenylene, and the like. Preferable is 1,4-phenylene.

The term "heteroarylene" herein used means a divalent group of the above-mentioned "heteroaryl". Examples of the heteroarylene are thiophene-diyl, furan-diyl, pyridine-diyl, and the like. Preferable is 2,5-thionphene-diyl, 2,5-furan-diyl, and the like.

In the present specification, the term "acyl" employed alone or in combination with other terms includes alkylcarbonyl in which alkyl group is the above-mentioned "lower alkyl" and arylcarbonyl in which aryl group is the above-mentioned "aryl". Examples of the acyl are acetyl, propionyl, benzoyl, and the like. "Lower alkyl" and "aryl" may be substituted respectively with substituents mentioned below.

The term "halogen" herein used means fluoro, chloro, bromo, and iodo. Fluoro, chloro, and bromo are preferred.

The term "lower alkyloxy" herein used are methyloxy, ethyloxy, n-propyloxy, isopropyloxy, n-butyloxy, isobutyloxy, sec-butyloxy, tert-butyloxy, and the like. Methyloxy, ethyloxy, n-propyloxy, isopropyloxy and n-butyloxy are preferred.

The term "lower alkylthio" herein used are methylthio, ethylthio, and the like.

The term "lower alkenyloxy" herein used are vinyloxy, aryloxy, propenyloxy, crotonyloxy, isopentenyloxy and the like.

The term "lower alkyloxycarbonyl" herein used are methyloxycarbonyl, ethyloxycarbonyl, n-propyloxycarbonyl, isopropyloxycarbonyl, and the like.

In the present specification, the term "halo(lower)alkyl" employed alone or in combination with other terms includes the above-mentioned "lower alkyl" which is substituted with the above mentioned "halogen" at 1 to 8 positions, preferably, at 1 to 5. Examples of the halo(lower)alkyl are trifluoromethyl, trichloromethyl, difluoroethyl, trifluoroethyl, dichloroethyl, trichloroethyl, and the like. Preferable is trifluoromethyl.

Examples of the term "halo(lower)alkyloxy" herein used are trifluoromethyloxy and the like.

Examples of the term "lower alkylsulfonyl" herein used are methylsulfonyl, ethylsulfonyl and the like. Preferable is methylsulfonyl.

Examples of the term "acyloxy" herein used are acetyloxy, propionyloxy, benzoyloxy and the like.

In the present specification, the term "optionally substituted amino" includes amino or amino substituted with one or two of the above mentioned "lower alkyl", "aralkyl", "heteroarylalkyl" or "acyl". Examples of the optionally substituted amino are amino, methylamino, dimethylamino, ethylmethylamino, diethylamino, benzylamino, acetylamino, benzoylamino and the like. Preferable are amino, methylamino, dimethylamino, ethylmethylamino, diethylamino and acetylamino.

Examples of the term "optionally substituted aminocarbonyl" herein used are aminocarbonyl, methylaminocarbonyl, dimethylaminocarbonyl, ethylmethylaminocarbonyl, diethylaminocarbonyl and the like. Preferable is aminocarbonyl, diethylaminocarbonyl.

The substituents of "optionally substituted lower alkyl" are cycloalkyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted non-aromatic heterocyclic group, aryloxy (e.g., phenyloxy), aralkyloxy (e.g., benzyloxy), lower alkylsulfonyl, guanidino, azo group, optionally substituted ureide and the like. These substituents are able to locate at one or more of any possible positions.

Preferable are carboxy, carbamoyl, lower alkylthio, hydroxy, lower alkyloxy as substituents of "optionally substituted lower alkyl" for $R^2$.

Preferable are hydroxy, lower alkyloxy, optionally substituted non-aromatic heterocyclic group as substituents of "optionally substituted lower alkyl" for $R^3$.

The substituents of "optionally substituted arylene", "optionally substituted heteroarylene", "optionally substituted aryl", "optionally substituted heteroaryl", "optionally substituted non-aromatic heterocyclic group", "optionally substituted aralkyl", "optionally substituted heteroarylalkyl", and "optionally substituted ureide" herein used are optionally substituted lower alkyl, cycloalkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy, optionally substituted aryl, optionally substituted heteroaryl, optionally substituted non-aromatic heterocyclic group, optionally substituted aralkyl, lower alkylsulfonyl, guanidino group, azo group, or optionally substituted ureide, carbamoyl, lower alkenyloxy and the like. These substituents are able to locate at one or more of any possible positions.

Substituents of "optionally substituted arylene" and "optionally substituted heteroarylene" for $R^4$ herein used are halogen, nitro, cyano, lower alkyloxy, and the like. Preferable are unsubstituted "arylene" and unsubstituted "heteroarylene".

Substituents of "optionally substituted aryl" for $R^2$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower) alkyl, halo(lower) alkyloxy, optionally substituted amino, optionally substituted aminocarbonyl, acyl, acyloxy and the like. Preferable are aryl optionally substituted with hydroxy.

Substituents of "optionally substituted aryl" for $R^3$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable is aryl optionally substituted with hydroxy, lower alkyloxy, halogen, or halo(lower)alkyl.

Substituents of "optionally substituted aryl" for $R^6$ herein used are optionally substituted lower alkyl, cycloalkyl, lower alkenyl, lower alkynyl, hydroxy, lower alkyloxy, lower alkenyloxy, mercapto, lower alkylthio, halogen, nitro, cyano, carboxy, carbamoyl, lower alkyloxycarbonyl, halo(lower)alkyl, halo(lower)alkyloxy, optionally substituted amino, optionally substituted aminocarbonyl, acyl, acyloxy and the like. Preferable are halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, optionally substituted amino and the like as a substituent. Preferable are aryl optionally substituted with lower alkyl, lower alkyloxy, halogen, lower alkylthio, or optionally substituted amino.

Substituents of "optionally substituted heteroaryl" for $R^2$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable are heteroaryl optionally substituted with hydroxy or halogen.

Substituents of "optionally substituted heteroaryl" for $R^3$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo (lower)alkyloxy, optionally substituted amino, optionally substituted aminocarbonyl, acyl, acyloxy and the like. Preferable are heteroaryl optionally substituted with hydroxy, lower alkyloxy, halogen or halo(lower)alkyl.

Substituents of "optionally substituted heteroaryl" for $R^6$ herein used are optionally substituted lower alkyl, cycloalkyl, lower alkenyl, lower alkynyl, hydroxy, lower alkyloxy, lower alkenyloxy, mercapto, lower alkylthio, halogen, nitro, cyano, carboxy, carbamoyl, lower alkyloxycarbonyl, halo(lower)alkyl, halo(lower)alkyloxy, optionally substituted amino, optionally substituted aminocarbonyl, acyl, acyloxy and the like. Preferable are halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, optionally substituted amino as a substituent. Preferable are heteroaryl optionally substituted with lower alkyl, lower alkyloxy, halogen, lower alkylthio, or optionally substituted amino.

Substituents of "optionally substituted aralkyl" for $R^2$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable are aryl optionally substituted with hydroxy.

Substituents of "optionally substituted aralkyl" for $R^3$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable are aralkyl optionally substituted with hydroxy, lower alkyloxy, halogen, or halo(lower)alkyl.

Substituents of "optionally substituted heteroarylalkyl" for $R^2$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable are heteroarylalkyl optionally substituted with halogen or hydroxy.

Substituents of "optionally substituted heteroarylalkyl" for $R^3$ herein used are optionally substituted lower alkyl, lower alkenyl, lower alkynyl, hydroxy, lower alkyloxy, mercapto, lower alkylthio, halogen, nitro, cyano, carboxy, lower alkyloxycarbonyl, halo(lower)alkyl, halo(lower)alkyloxy, optionally substituted amino, optionally substituted aminocarbonyl, acyl, acyloxy and the like. Preferable are heteroaryl alkyl optionally substituted with hydroxy, lower alkyloxy, halogen, or halo(lower)alkyl.

Substituents of "optionally substituted non-aromatic heterocyclic group" for $R^6$ herein used are optionally substituted lower alkyl, cycloalkyl, lower alkenyl, lower alkynyl, hydroxy, lower alkyloxy, lower alkenyloxy, mercapto, lower alkylthio, halogen, nitro, cyano, carboxy, carbamoyl, lower alkyloxycarbonyl, halo(lower)alkyl, halo(lower) alkyloxy, optionally substituted amino, optionally substituted aminocarbonyl, acyl, acyloxy and the like. Preferable are halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, or optionally substituted amino and the like. Preferable is optionally substituted non-aromatic heterocyclic group optionally substituted with lower alkyl, lower alkyloxy, halogen, lower alkylthio, or optionally substituted amino.

A compound of the present invention has excellent inhibitory activities against plural MMPs (e.g., MMP-2, MMP-8, MMP-9, MMP-12, MMP-13) and preferable is a compound represented by the formula:

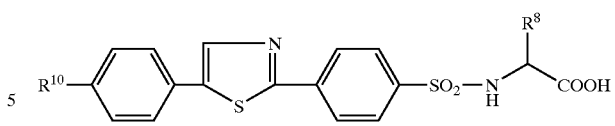

wherein $R^8$ is hydrogen atom, methyl, isopropyl, isobutyl, carboxymethyl, carboxyethyl, 2-methylthioethyl, benzyl, 4-hydroxybenzyl, or indol-3-ylmethyl: $R^{10}$ is hydrogen atom, halogen, lower alkyl, lower alkyloxy, halo(lower) alkyl, acyl, nitro, cyano, optionally substituted amino, or hydroxy.

BEST MODE FOR CARRYING OUT THE INVENTION

Compounds (I) of the present invention are able to be synthesized in accordance with the procedure described in WO97/27174 and WO99/4780. Syntheses are explained in detail below.

Method A

For example, a compound represented by the formula (I) is able to be prepared by the following method.

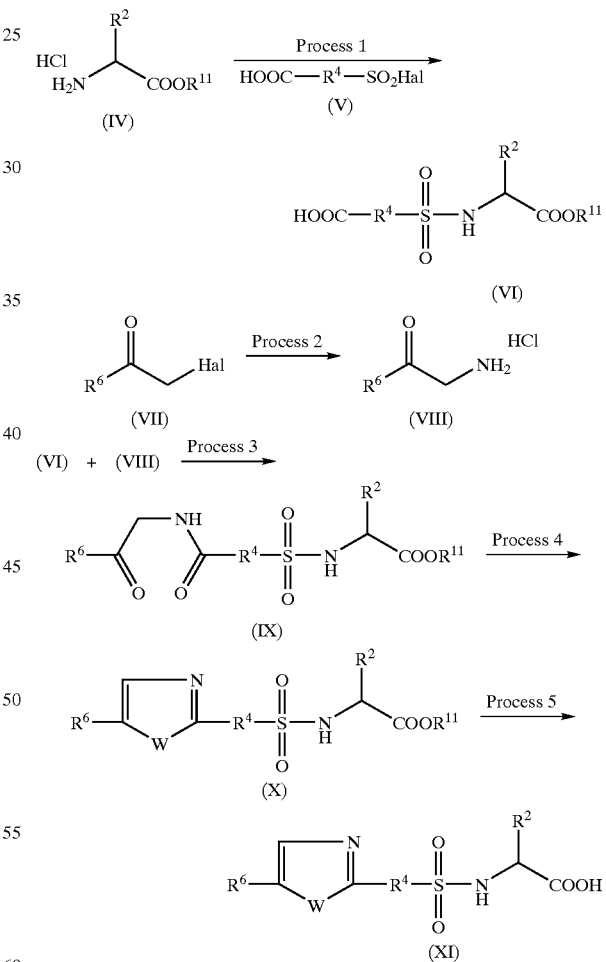

wherein $R^2$, $R^4$, and $R^6$ are as defined above, $R^{11}$ is a protecting group of a carboxyl group; Hal is each independently halogen; W is oxygen or sulfur atom.

(Process 1)

This process can be accomplished in accordance with the process 1 in the method A described in WO97/27174.

(Process 2)

Compound (VII) is dissolved in a solvent such as chloroform, dichloromethane. An amine such as hexamethylenetetramine is added. The mixture is stirred at 0° C. to 60° C., preferably 10° C. to 40° C. for 1 to 48 h, preferably 10 to 30 h. The obtained quaternary ammonium salt is suspended in a solvent such as methanol, ethanol. Concentrated hydrochloric acid is added thereto. The mixture is stirred at 0° C. to 60° C., preferably 10° C. to 40° C. for 1 to 48 h, preferably 10 to 30 h to give a primary ammonium hydrochloride (VIII).

(Process 3)

Compound (VI) and dimethylformamide are suspended in a solvent such as dichloromethane. A halogenating agent such as oxalyl chloride is added thereto at −30° C. to 20° C., preferably at −10° C. to 5° C. The suspension is stirred for 10 min to 3 h, preferably for 30 min to 2 h to give the acid halide of compound (VI). Compound (VIII) and pyridine or N-methylmorpholine are suspended in a solvent such as dichloromethane. The above obtained solution containing the acid halide is added to the suspension at −30° C. to 30° C., preferably at −10° C. to 10° C. The mixture is stirred at 0° C. to 50° C., preferably at 10° C. to 40° C. for 1 h to 24 h, preferably for 2 h to 5 h to give compound (IX).

(Process 4)

In a case of preparing a compound in which W is oxygen, compound (IX) is suspended in phosphorus oxychloride. The mixture is stirred at 70° C. to 150° C., preferably at 90° C. to 120° C. for 1 h to 5 h, preferably for 1 h to 2 h to give compound (X).

In a case of preparing a compound in which W is sulfur, compound (IX) is dissolved in a solvent such as tetrahydrofuran and the like. Lawesson's reagent is added. The mixture is stirred at 40° C. to 100° C., preferably at 60° C. to 90° C. for 1 h to 5 h, preferably for 1 h to 3 h to give compound (X).

(Process 5)

This process can be accomplished in accordance with the process 1 in the method A described in WO97/27174.

In accordance with the method described in WO97/27174, the obtained compound (X) can be converted to a compound, which has a hydroxamic acid group or is substituted with $R^3$ at the nitrogen atom.

The term "solvate" in the present invention herein used includes a solvate with an organic solvent(s), a hydrate and the like. These hydrates can coordinate with any water molecules.

The term "compound of the present invention" herein used includes a pharmaceutically acceptable salt or its solvate. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts and solvates can be formed by the usual method.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985. For instance, prodrugs such as an ester derivative, optionally substituted alkyloxycarbonyl, which is prepared by reacting a basal acid compound with a suitable alcohol, or an amide derivative, optionally substituted alkylaminocarbonyl, which is prepared by reacting a basal acid compound with a suitable amine are exemplified when the compounds according to present invention have a carboxylic group. Particularly preferred esters as prodrugs are methyl ester, ethyl ester, n-propyl ester, isopropyl ester, n-butyl ester, isobutyl ester, tert-butyl ester, morpholinoethyl ester, and N,N-diethylglycolamido ester, and the like. For instance, prodrugs such as an acyloxy derivative which is prepared by reacting a basal hydroxy compound with a suitable acyl halide or a suitable acid anhydride are exemplified when the compounds according to present invention have a hydroxy group. Particularly preferred acyloxy derivatives as prodrugs —$OCOC_2H_5$, —$OCO(t\text{-}Bu)$, —$OCOC_{15}H_{31}$, —$OCO(m\text{-}COONa\text{-}Ph)$, —$OCOCH_2CH_2COONa$, —$OCOCH(NH_2)CH_3$, —$OCOCH_2N(CH_3)_2$, and the like. For instance, prodrugs such as an amide derivative which is prepared by reacting a basal amino compound with a suitable acid halide or a suitable acid anhydride are exemplified when the compounds according to present invention have an amino group. Particularly preferred amide as prodrugs are —$NHCO(CH_2)_{20}CH_3$, —$NHCOCH(NH_2)CH_3$, and the like.

The compound of the present invention is not restricted to any particular isomers but includes all possible isomers and racemic modifications.

The compound of the present invention has excellent inhibitory activities against MMPs, as described in the following test example.

Definitely, the compounds of the present invention are useful in the treatment of diseases such as chronic obstructive pulmonary disease, osteoarthritis, rheumatoid arthritis, corneal ulceration, periodontal disease, advanced virus infection (e.g., HIV infection), arteriosclerosis obliterans, arteriosclerotic aneurysm, aortic aneurysm, atherosclerosis, restenosis, sepsis, septic shock, coronary thrombosis, aberrant angiogenesis, scleritis, multiple sclerosis, hepatocirrhosis, open angle glaucoma, retinopathies (e.g., diabetic retinopathy), proliferative retinopathy, neovascular glaucoma, pterygium, keratitis, epidermolysis bullosa, psoriasis, diabetes, nephritis, neurodegengerative disease, inflammation, osteoporosis, deossification, gingivitis, tumor growth, tumor angiogenesis, ocular tumor, angiofibroma, hemangioma, fever, hemorrhage, coagulation, cachexia, anorexia, acute infection, shock, autoimmune disease, malaria, Crohn disease, meningitis, heart failure, asthmatic respiratory tract disease, arteriosclerosis, cancer and gastric ulcer.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 0.1 to 20 mg/kg/day for adult.

The following examples and test examples are provided to further illustrate the present invention and are not to be constructed as limiting the scope thereof.

Abbreviations described below are used in the following examples.

| | |
|---|---|
| Me: | methyl |
| Et: | ethyl |
| n-Pr: | n-propyl |
| i-Pr: | isopropyl |
| n-Bu: | n-butyl |
| i-Bu: | isobutyl |
| t-Bu: | tert-butyl |
| Ph: | phenyl |
| Bn: | benzyl |
| DMSO: | dimethyl sulfoxide |

EXAMPLE

Example 1

The Preparation of the Compound (A-1)

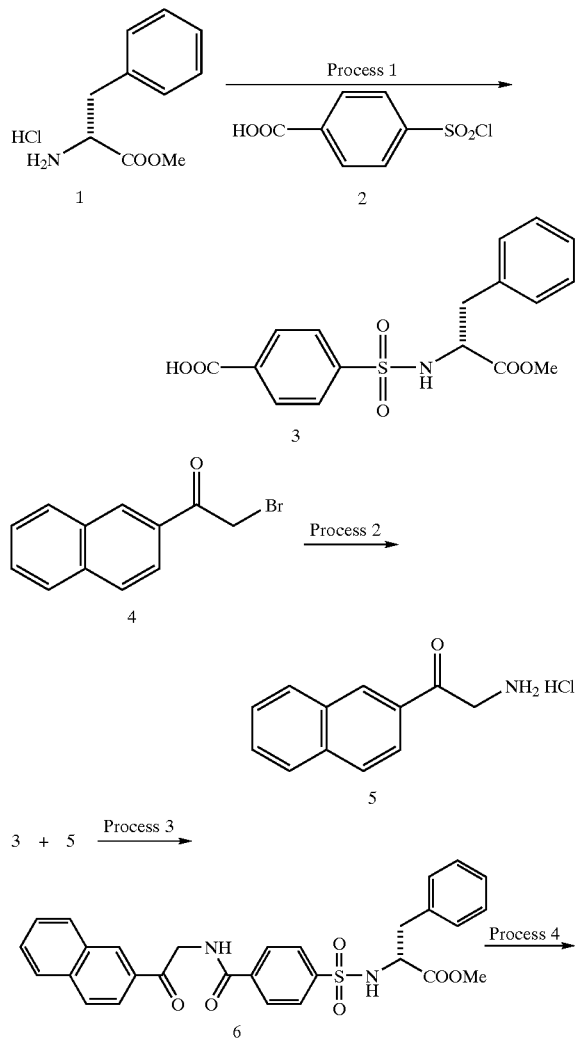

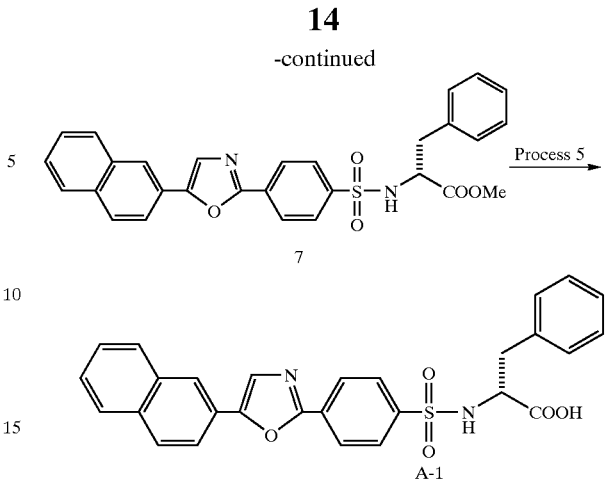

(Process 3)

To a solution of D-phenylalanine methyl ester hydrochloric acid salt (1, 18.12 g, 84 mmol) in water (100 ml) were added 2 mol/L aqueous sodium carbonate solution (61.25 ml) and 4-chlorosulfonylbenzoic acid (2, 16.09 g,70 mmol) and the mixture was stirred at a room temperature for 3 h, poured to ice-hydrochloric acid (2 mol/L) and extracted with ethyl acetate. The organic layer was washed with brine, dried over anhydrous sodium sulfate and concentrated under a reduced pressure. The residue was crystallized from acetone/hexane to give a desired product (3, 21.56 g, yield 84.8%). m.p. 188–189° C.

IR (KBr, vmax cm$^{-1}$) 3280, 2956, 1737, 1691, 1428, 1346, 1284, 1166, 723 $^1$H NMR (CDCl$_3$, δ ppm): 2.77(dd, J=9.3, 13.5 Hz, 1H), 2.94 (dd, J=5.7, 13.5 Hz, 1H), 3.37 (s, 3H), 4.01 (dt, J=6.0, 9.0 Hz, 1H), 7.08–7.23 (m, 5H), 7.66 (d, J=8.4 Hz, 2H), 7.97 (d, J=8.4 Hz, 2H), 8.69 (d, J=9.0 Hz, 1H), 13.38 (br s, 1H) $[\alpha]_D$+3.2±0.9 (c=0.505, DMSO, 24° C.) Elemental analysis (C$_{17}$H$_{17}$NO$_6$S) Calcd.: C, 56.19; H, 4.72; N, 3.85; S, 8.82. Found: C, 56.06; H, 4.57; N, 3.93; S, 8.75.

(Process 2)

A solution of 2-bromoacetylnaphthalene (4, 4.98 g, 20 mmol) and hexamethylenetetramine (3.08 g, 22 mmol) in chloroform (60 ml) was stirred at a room temperature for 24 h. The obtained crystals were collected by filtration, washed with chloroform to give the salt of hexamethylenetetramine (7.66 g). A part of the salt (6.38 g) was suspended in ethanol (60 ml). Concentrated hydrochloric acid (15 ml) was added at a room temperature and the mixture was stirred for 24 h. Obtained crystals was filtered and washed with water to give a desired product (5, 3.10 g, yield 84%) with decomposition point more than 200° C.

IR (KBr, ν max cm$^{-1}$) 3442, 2940, 2842, 1689, 1619, 1479, 1386, 1261, 1189, 1120, 817 $^1$H NMR (DMSO-d$_6$, δ ppm): 4.72 (s, 2H), 7.64–7.77 (m, 2H), 7.99–8.12 (m, 3H), 8.17 (d, J=7.8 Hz, 1H), 8.57 (s, 3H), 8.79 (s, 1H) HR-FABMS m/z Salt free amine C$_{12}$H$_{12}$NO [M+H]$^{+\ Calcd}$: 186.0919. Found: 186.0920.

(Process 3)

Oxalyl chloride (105 μl, 1.2 mmol) was added to a suspension of compound (3) (363 mg, 1 mmol) and dimethylformamide (0.05 ml) in dichloromethane (3 ml) with cooling in ice. The mixture was stirred at a room temperature for 1 h. The acid chloride solution obtained above was added to a suspension of compound (5) (244 mg, 1.1 mmol) and pyridine (0.28 ml, 3.5 mmol) in dichloromethane (3 ml) with cooling in ice. The mixture was stirred at a room temperature for 3 h and poured to ice-2N hydrochloric acid and extracted with ethyl acetate. The organic layer was washed with saturated aqueous sodium hydrogencarbonate solution and brine successively, dried over anhydrous sodium sulfate and concentrated under a reduced pressure. The crystalline residue obtained (6, 540 mg) was used to the next reaction without further purification.

(Process 4)

A suspension of compound (6) and phosphorus oxychloride (6 ml) was stirred at 110° C. for 1.5 h and concentrated under a reduced pressure. Ice was added to the residue. The mixture was extracted with ethyl acetate. The organic phase was washed with saturated aqueous sodium hydrogencarbonate solution and brine successively, dried over anhydrous sodium sulfate and concentrated under a reduced pressure. The residue was chromatographed on silica gel in chloroform/ethyl acetate=3/2 and crystallized from acetone/hexane to give a desired product (7, 212 mg, yield of two steps, 41.4%) with a melting point of 176–178° C.

IR (KBr, ν max cm$^{-1}$) 3345, 1743, 1342, 1176, 1164, 1095, 817, 752 $^1$H NMR (DMSO-$d_6$, δ ppm): 3.04 and 3.10 (dABq, J=6.0, 13.8 Hz, 2H), 3.54 (s, 3H), 4.29 (dt, J=9.3, 6.0 Hz, 1H), 5.15 (d, J=9.3 Hz, 1H), 7.05–7.12 (m, 2H), 7.21–7.30 (m, 3H), 7.49–7.60 (m, 2H), 7.61 (s, 1H), 7.79 (dd, J=0.9, 8.4 Hz, 1H), 7.87 (d, J=8.1 Hz, 4H), 7.93 (d, J=8.4 Hz, 1H), 8.21–8.25 (m, 3H) $[\alpha]_D$-12.9±1.0 (c=0.506, DMSO, 24° C.) Elemental analysis ($C_{29}H_{24}N_2O_5S$.0.4 acetone) Calcd.: C, 67.70; H, 4.97; N, 5.23; S, 5.98. Found: C, 67.43; H, 4.75; N, 5.38; S, 6.26.

(Process 5)

1 Mol/L of aqueous sodium hydroxide solution (1.0 ml) was added to a solution of compound (7) (170 mg, 0.332 mmol) in dimethylsulfoxide (4 ml) at a room temperature and the mixture was stirred for 24 h. The precipitated sodium salt was collected by filtration, poured to ice-2 mol/L hydrochloric acid and extracted with ethyl acetate. The organic phase was washed with brine, dried over anhydrous sodium sulfate and concentrated under a reduced pressure. The residue was crystallized from acetone/hexane to give a desired product (A-1, 119 mg, yield 71.9%) with a melting point of 243–245° C.

IR (KBr, ν max cm$^{-1}$) 3430, 3284, 1718, 1344, 1261, 1166, 1095, 846 $^1$H NMR (DMSO-$d_6$, δ ppm): 2.76(dd, J=9.3, 13.5 Hz, 1H), 2.99 (dd, J=5.1, 13.5 Hz, 1H), 3.97 (dt, J=5.7, 9.0 Hz, 1H), 7.11–7.26 (m, 5H), 7.54–7.65 (m, 2H), 7.76 (d, J=8.7 Hz, 2H), 7.98 (dd, J=2.1, 8.4 Hz, 1H), 8.01–8.10 (m, 4H), 8.18 (d, J=8.7 Hz, 2H), 8.44–8.53 (m, 2H), 12.80 (br s, 1H) $[\alpha]_D$-5.9±0.9 (c=0.508, DMSO, 24.5° C.) Elemental analysis ($C_{28}H_{22}N_2O_5S$.0.2$H_2O$) Calcd: C, 66.97; H, 4.50; N, 5.58; S, 6.39. Found: C, 66.99; H, 4.34; N, 5.63; S, 6.24.

The following compounds (A-2) to (A-51) were synthesized in a manner similar to Example 1. Their results were shown in Table 1 to Table 7.

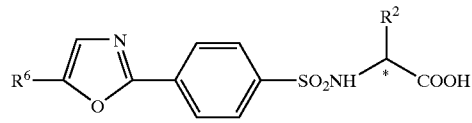

The mark * shows to be an optically active form unless $R^2$ is hydrogen atom and the absolute configuration was displayed in the table.

TABLE 1

| Example No. | Compound No. | $R^2$ | $R^6$ | * | $^1$H-NMR (DMSO-$d_6$) |
|---|---|---|---|---|---|
| 2 | A-2 | Me | phenyl | R | 1.20 (d, J=7.2 Hz, 3H), 3.85 (m, 1H), 7.43 (m, 1H), 7.54 (t, J=7.5 Hz, 2H), 7.89 (d, J 7.5=Hz, 2H), 7.94 (s, 1H), 7.96 (d, J=8.1 Hz, 2H), 8.27 (d, J=8.1 Hz, 2H), 8.35 (d, 8.4 Hz, 1H), 12.67 (br s, 1H) |
| 3 | A-3 | Me | phenyl | S | 1.20 (d, J=7.2 Hz, 3H), 3.85 (m, 1H), 7.43 (m, 1H), 7.54 (t, J=7.8 Hz, 2H), 7.89 (d, J=8.1 Hz, 2H), 7.94 (s, 1H), 7.96 (d, J=8.1 Hz, 2H), 8.27 (d, J=8.1 Hz, 2H), 8.33 (d, 8.1 Hz, 1H), 12.66 (br s, 1H) |
| 4 | A-4 | Me | 4-Cl-phenyl | R | 1.19 (d, J=7.5 Hz, 3H), 3.84 (m, 1H), 7.60 (d, J=8.7 Hz, 2H), 7.92 (d, J=9.0 Hz, 2H), 7.95 (d, J=8.7 Hz, 2H), 7.99 (s, 1H), 8.27 (d, J=8.7 Hz, 2H), 8.33 (m, 1H), 12.60 (br s, 1H) |
| 5 | A-5 | Me | 4-Cl-phenyl | S | 1.19 (d, J=7.5 Hz, 3H), 3.84 (m, 1H), 7.58–7.63 (m, 2H), 7.89–7.98 (m, 4H), 7.99 (s, 1H), 8.24–8.29 (m, 2H), 8.33 (d, J=8.1 Hz, 1H), 12.62 (br s, 1H) |
| 6 | A-6 | Me | 4-F-phenyl | R | 1.19 (d, J=7.5 Hz, 3H), 3.84 (m, 1H), 7.92 (s, 1H), 7.95 (m, 2H), 7.95 (d, J=8.4 Hz, 2H), 8.26 (d, J=8.7 Hz, 2H), 8.35 (d, J=8.1 Hz, 1H), 12.61 (br s, 1H) |
| 7 | A-7 | Me | 4-F-phenyl | S | 1.19 (d, J=7.5 Hz, 3H), 3.85 (m, 1H), 7.39 (t, J=8.7 Hz, 2H), 7.91–7.99 (m, 5h), 8.26 (d, J=8.7 Hz, 2H), 8.35 (d, J=7.8 Hz, 1H), 12.68 (br s, 1H) |

TABLE 1-continued

| Example No. | Compound No. | R² | R⁶ | * | ¹H-NMR (DMSO-d₆) |
|---|---|---|---|---|---|
| 8 | A-8 | Me | MeO-C₆H₄- | R | 1.19 (d, J=7.2 Hz, 3H), 3.83 (s, 3H), 3.83 (m, 1H), 7.09 (d, J=9.0 Hz, 2H), 7.79 (s, 1H), 7.82 (d, J=9.0 Hz, 2H), 7.94 (d, J=8.7 Hz, 2H), 8.23 (d, J=8.4 Hz, 2H), 8.32 (d, J=6.9 Hz, 1H) |
| 9 | A-9 | Me | MeO-C₆H₄- | S | 1.19 (d, J=7.2 Hz, 3H), 3.83 (a, 3H), 3.84 (m, 1H), 7.06–7.12 (m, 2H), 7.79 (s, 1H), 7.79-7.85 (m, 2H), 7.91–7.97 (m, 2H), 8.21–8.26 (m, 2H), 8.33 (d, J=8.4 Hz, 1H), 12.65 (br s, 1H) |
| 10 | A-10 | Me | Br-C₆H₄- | R | 1.19 (d, J=7.2 Hz, 3H), 3.84 (m, 1H), 7.74 (d, J=8.4 Hz, 2H), 7.85 (d, J=8.4 Hz, 2H), 7.95 (d, J=8.1 Hz, 2H), 8.00 (a, 1H), 8.27 (d, J=8.1 Hz, 2H), 8.34 (br s, 1H), 12.70 (br s, 1H) |

TABLE 2

| Example No. | Compound No. | R² | R⁶ | * | ¹H-NMR (DMSO-d₆) |
|---|---|---|---|---|---|
| 11 | A-11 | Me | Br-C₆H₄- | S | 1.19 (d, J=7.2 Hz, 3H), 3.84 (in, 1H), 7.74 (d, J=8.7 Hz, 2H), 7.86 (d, J=9.0 Hz, 2H), 7.95 (d, J=8.7 Hz, 2H), 8.01 (s, 1H), 8.27 (d, J8.7 Hz, 2H), 8.35 (br s, 1H), 12.70 (br s, 1H) |
| 12 | A-12 | Bn | C₆H₅- | R | 2.75 (dd, J=9.3, 13.8 Hz, 1H), 2.94 (dd, J=5.4, 13.8 Hz, 1H), 3.95 (dt, J=5.7, 8.7 Hz, 1H), 7.11–7.24 (m, 5H), 7.43 (m, 1H), 7.54 (t, J=7.2 Hz, 2H), 7.72 (d, J=8.1 Hz, 2H), 7.89 (d, J=7.5 Hz, 2H), 7.94 (s, 1H), 8.11 (d, J=8.1 Hz, 2H), 8.49 (d, J=9.3 Hz, 1H), 12.79 (br s, 1H) |
| 13 | A-13 | Bn | C₆H₅- | S | 2.75 (dd, J=9.6, 13.8 Hz, 1H), 2.98 (dd, J=5.7, 13.8 Hz, 1H), 3.95 (dt, J=5.4, 9.0 Hz, 1H), 7.10–7.25 (m, 5H), 7.43 (m, 1H), 7.54 (t, J=7.2 Hz, 2H), 7.73 (d, J=8.4 Hz, 2H), 7.89 (d, J=7.2 Hz, 2H), 7.94 (s, 1H), 8.12 (d, J=8.4 Hz, 2H), 8.47 (d, J=8.7 Hz, 1H), 12.77 (br s, 1H) |
| 14 | A-14 | Bn | MeO-C₆H₄- | R | 2.75 (dd, Jz=9.3, 13.5 Hz, 1H), 2.97 (dd, J=5.4, 13.8 Hz, 1H), 3.83 (s, 3H), 3.94 (dt, J=5.4, 9.0 Hz, 1H), 7.10 (d, J=9.0 Hz, 2H), 7.12–7.24 (m, 5H), 7.71 (d, J=8.4 Hz, 2H), 7.78 (s, 1H), 7.82 (d, J=9.0 Hz, 2H), 8.09 (d, J=8.4 Hz, 2H), 8.47 (d, J=9.0 Hz, 1H), 12.76 (br s, 1H) |
| 15 | A-15 | Bn | Cl-C₆H₄- | R | 2.74 (dd, J=9.3, 13.8 Hz, 1H), 2.97 (dd, J=5.4, 13.8 Hz, 1H), 3.94 (m, 1H), 7.10–7.25 (m, 5H), 7.61 (d, J=8.7 Hz, 2H), 7.72 (d, J=8.7 Hz, 2H), 7.92 (d, J=8.7 Hz, 2H), 7.99 (s, 1H), 8.12 (d, J=8.7 Hz, 2H), 8.49 (d, J=9.9 Hz, 1H) |
| 16 | A-16 | Bn | Cl-C₆H₄- | S | 2.75 (dd, J=9.3, 13.8 Hz, 1H), 2.98 (dd, J=5.7, 13.8 Hz, 1H), 3.95 (m, 1H), 7.11–7.23 (m, 5H), 7.58–7.64 (m, 2H), 7.72 (d, J=8.4 Hz, 2H), 7.90–7.95 (m, 2H), 7.99 (s, 1H), 8.12 (d, J=8.4 Hz, 2H), 8.49 (d, J=8.4 Hz, 1H), 12.80 (br s, 1H) |
| 17 | A-17 | Bn | Br-C₆H₄- | R | 2.74 (dd, J=9.3, 13.8 Hz, 1H), 2.97 (dd, J=5.7, 13.8 Hz, 1H), 3.94 (m, 1H), 7.11–7.22 (m, 5H), 7.71 (d, J=7.5 Hz, 2H), 7.70–7.75 (m, 2H), 7.83–7.87 (m, 2H), 8.00 (s, 1H), 8.12 (d, J=8.4 Hz, 2H), 8.48 (d, J=9.0 Hz, 2H), 12.78 (br s, 1H) |

TABLE 3

| Example No. | Compound No. | $R^2$ | $R^6$ | * | $^1$H-NMR (DMSO-$d_6$) |
|---|---|---|---|---|---|
| 18 | A-18 | Bn | Br-C$_6$H$_4$- (4-bromophenyl) | S | 2.74 (dd, J=9.3, 13,8 Hz, 1H), 2.97 (dd, J=5.1, 13.5 Hz, 1H), 3.93 (m, 1H), 7.11–7.22 (m, 5H), 7.71 (d, J=7.8 Hz, 2H), 7.74 (d, J=8.4 Hz, 2H), 7.85 (d, J=8.7 Hz, 2H), 8.00 (s, 1H), 8.12 (d, J=8.4 Hz, 2H), 8.49 (d, J=9.3 Hz, 1H), 12.80 (br s, 1H) |
| 19 | A-19 | Bn | F-C$_6$H$_4$- (4-fluorophenyl) | R | 2.72 (dd, J=9.3, 13.8 Hz, 1H), 2.97 (dd, J=5.7, 13.8 Hz, 1H), 3.95 (m, 1H), 7.10–7.24 (m, 5H), 7.39 (t, J=8.7 Hz, 2H), 7.72 (d, J=8.4 Hz, 2H), 7.92 (s, 1H), 7.92–7.99 (m, 2H), 8.12 (d, J=8.4 Hz, 2H), 8.48 (d, J=9.0 Hz, 1H), 12.78 (br s, 1H) |
| 20 | A-20 | Bn | F-C$_6$H$_4$- (4-fluorophenyl) | S | 2.74 (dd, J=9.6, 14.1 Hz, 1H), 2.97 (dd, J=5.7, 13.8 Hz, 1H), 3.90 (m, 1H), 7.10–7.24 (m, 5H), 7.39 (t, J=9.0 Hz, 2H), 7.71 (d, J=8.4 Hz, 2H), 7.92 (s, 1H), 7.93–7.98 (m, 2H), 8.11 (d, J=8.4 Hz, 2H), 8.49 (d, J=9.0 Hz, 1H), 12.80 (br s, 1H) |
| 21 | A-21 | i-Pr | C$_6$H$_5$- (phenyl) | R | 0.81 (d, J=6.6 Hz, 3H), 0.84 (d, J=6.6 Hz, 3H), 1.96 (m, 1H), 3.58 (dd, J=6.0, 9.3 Hz, 1H), 7.43 (m, 1H), 7.53 (t, J=7.2 Hz, 2H), 7.86–7.97 (m, 5H), 8.22 (d, J=9.3 Hz, 1H), 8.25 (d, J=8.7 Hz, 2H), 12.61 (br s, 1H) |
| 22 | A-22 | i-Pr | C$_6$H$_5$- (phenyl) | S | 0.81 (d, J=6.9 Hz, 3H), 0.85 (d, J=6.9 Hz, 3H), 1.97 (m, 1H), 3.58 (dd, J=6.3, 8.4 Hz, 1H, 7.43 (m, 1H), 7.53 (t, J=7.2 Hz, 2H), 7.89 (d, J=7.8 Hz, 2H), 7.94 (d, J=8.4 Hz, 2H), 7.94 (s, 1H), 8.21 (d, J=8.4 Hz, 1H), 8.25 (d, J=8.4 Hz, 2H), 12.60 (br s, 1H) |
| 23 | A-23 | i-Pr | Cl-C$_6$H$_4$- (4-chlorophenyl) | R | 0.81 (d, J=6.6 Hz, 3H), 0.84 (d, J, 6.9 Hz, 3H), 1.96 (m, 1H), 3.57 (m, 1H), 7.60 (d, J=8.7 Hz, 2H), 7.93 (d, J=9.0 Hz, 2H), 7.94 (d, J=8.7 Hz, 2H), 7.99 (s, 1H), 8.22 (m, 1H), 8.25 (d, J=8.7 Hz, 2H), 12.61 (br s, 1H) |
| 24 | A-24 | i-Pr | Cl-C$_6$H$_4$- (4-chlorophenyl) | S | 0.81 (d, J=6.9 Hz, 3H), 0.84 (d, J=, 6.9 Hz, 3H), 1.97 (m, 1H), 3.57 (m, 1H), 7.60 (d, J=8.7 Hz, 2H), 7.58–7.63 (m, 2H), 7.90–7.97 (m, 2H), 7.99 (s, 1H), 8.18–8.29 (m, 3H), 12.60 (br s, 1H) |

TABLE 4

| Example No. | Compound No. | $R^2$ | $R^6$ | * | $^1$H-NMR (DMSO-$d_6$) |
|---|---|---|---|---|---|
| 25 | A-25 | i-Pr | F-C$_6$H$_4$- (4-fluorophenyl) | R | 0.81 (d, J=6.9 Hz, 3H), 0.84 (d, J=, 6.9 Hz, 3H), 1.97 (m, 1H), 3.58 (dd, J=5.7, 8.7 Hz, 1H), 7.39 (t, J=8.7 Hz, 2H), 7.91–7.99 (m, 5H), 8.20–8.28 (m, 3H), 12.62 (br s, 1H) |
| 26 | A-26 | i-Pr | F-C$_6$H$_4$- (4-fluorophenyl) | S | 0.81 (d, J=6.9 Hz, 3H), 0.84 (d, J=, 6.6 Hz, 3H), 1.96 (m, 1H), 3.57 (dd, J=6.0, 8.7 Hz, 1H), 7.39 (t, J=9.0 Hz, 2H), 7.91–7.99 (m, 5H), 8.22 (d, J=8.7 Hz, 1H), 8.24 (d, J=8.7 Hz, 2H), 12.62 (br s, 1H) |
| 27 | A-27 | i-Pr | Br-C$_6$H$_4$- (4-bromophenyl) | R | 0.81 (d, J=6.9 Hz, 3H), 0.84 (d, J=, 6.6 Hz, 3H), 1.96 (m, 1H), 3.57 (m, 1H), 7.70–7.76 (m, 2H), 7.83–7.88 (m, 2H), 7.93 (d, J=8.4 Hz, 2H), 8.00 (s, 1H), 8.18–8.29 (m, 3H) 12.65 (br s, 1H) |

TABLE 4-continued

| Example No. | Compound No. | R² | R⁶ | * | ¹H-NMR (DMSO-d₆) |
|---|---|---|---|---|---|
| 28 | A-28 | i-Bu | MeO–C₆H₄– | R | 0.73 (d, J=6.6 Hz, 3H), 0.83 (d, J=6.6 Hz, 3H), 1.32–1.50 (m, 2H), 1.60 (m, 1H), 3.71 (m, 1H), 3.83 (s, 3H), 7.09 (d, J=8.7 Hz, 2H), 7.79 (s, 1H), 7.83 (d, J=8.7 Hz, 2H), 7.92 (d, J=8.7 Hz, 2H), 8.23 (d, J=8.7 Hz, 2H), 8.33 (d, J=9.3 Hz, 1H), 12.61 (br s, 1H) |
| 29 | A-29 | i-Bu | MeO–C₆H₄– | S | 0.73 (d, J=6.6 Hz, 3H), 0.83 (d, J=6.6 Hz, 3H), 1.36–1.47 (m, 2H), 1.60 (m, 1H), 3.71 (m, 1H), 3.83 (s, 3H), 7.09 (d, J=9.0 Hz, 2H), 7.79 (s, 1H), 7.83 (d, J=9.0 Hz, 2H), 7.91 (d, J=8.7 Hz, 2H), 8.23 (d, J=8.4 Hz, 2H), 8.32 (d, J=8.1 Hz, 1H), 12.60 (br s, 1H) |
| 30 | A-30 | i-Bu | Cl–C₆H₄– | R | 0.73 (d, J=6.6 Hz, 3H), 0.83 (d, J=6.6 Hz, 3H), 1.33–1.50 (m, 2H), 1.60 (m, 1H), 3.72 (m, 1H), 7.57–7.63 (m, 2H), 7.89–7.96 (m, 4H), 7.99 (s, 1H), 8.24–8.29 (m, 2H), 8.35 (d, J=9.0 Hz, 1H), 12.61 (br s, 1H) |
| 31 | A-31 | i-Bu | Cl–C₆H₄– | S | 0.73 (d, J=6.6 Hz, 3H), 0.83 (d, J=6.9 Hz, 3H), 1.34–1.47 (m, 2H), 1.60 (m, 1H), 3.71 (m, 1H), 7.60 (d, J=8.4 Hz, 2H), 7.93 (d, J=8.7 Hz, 2H), 7.99 (s, 1H), 8.26 (d, J=8.4 Hz, 2H), 8.35 (m, 1H), 12.60 (br s, 1H) |

TABLE 5

| Example No. | Compound No. | R² | R⁶ | * | ¹H-NMR (DMSO-d₆) |
|---|---|---|---|---|---|
| 32 | A-32 | i-Bu | F–C₆H₄– | S | 0.73 (d, J=6.6 Hz, 3H), 0.83 (d, J=6.6 Hz, 3H), 1.34–1.50 (m, 2H), 1.60 (m, 1H), 3.71 (m, 1H), 7.40 (d, J=8.7 Hz, 2H), 7.91–7.98 (m, 5H), 8.26 (d, J=8.7 Hz, 2H), 8.35 (d, J=8.1 Hz, 1H), 12.65 (br s, 1H) |
| 33 | A-33 | s-Bu | Br–C₆H₄– | S | 0.75–0.83 (m, 6H), 1.14 (m, 1H), 1.37 (m, 1H), 1.69 (m, 1H), 3.60 (m, 1H), 7.73 (d, J=8.7 Hz., 2H), 7.86 (d, J=8.4 Hz, 2H), 7.93 (d, J=8.4 Hz, 2H), 7.97 (s, 1H), 8.25 (d, J=8.4 Hz, 2H), 12.60 (br s, 1H) |
| 34 | A-34 | s-Bu | MeO–C₆H₄– | S | 0.72–0.86 (m, 6H), 1.12 (m, 1H), 1.37 (m, 1H), 1.69 (m, 1H), 3.61 (m, 1H), 3.83 (s, 3H), 7.09 (d, J=9.0 Hz, 2H), 7.79 (s, 1H), 7.83 (d, J=8.4 Hz, 2H), 7.92 (d, J=8.4 Hz, 2H), 8.22 (d, J=8.7 Hz, 2H), 8.26 (m, 1H), 12.62 (br s, 1H) |
| 35 | A-35 | CH₃S—CH₂CH₂— | MeO–C₆H₄– | R | 165–1.95 (m, 2H), 1.94 (s, 3H), 2.26–2.48 (m, 2H), 3.83 (s, 3H), 3.91 (m, 1H), 7.09 (d, J=8.7 Hz, 2H), 7.79 (s, 1H), 7.83 (d, J=8.7 Hz, 2H), 7.92 (d, J=8.7 Hz, 2H), 8.23 (d, J=8.4 Hz, 2H), 8.38 (d, J=9.3 Hz, 1H), 12.81 (br s, 1H) |
| 36 | A-36 | CH₃S—CH₂CH₂— | Cl–C₆H₄– | R | 1.67–1.93 (m, 2H), 1.94 (s, 3H), 2.27–2.49 (m, 2H), 3.92 (m, 1H), 7.60 (d, J=8.4 Hz, 2H), 7.91–7.96 (m, 4H), 7.99 (s, 1H), 8.26 (d, J=8.4 Hz, 2H), 8.39 (d, J=8.4 Hz, 1H), 12.77 (br s, 1H) |
| 37 | A-37 | H | C₆H₅– | | 3.67 (d, J=4.5 Hz, 2H), 7.43 (m, 1H), 7.49–7.58 (m, 2H), 7.89 (d, J=7.2 Hz, 2H), 7.94 (s, 1H), 7.96 (d, J=8.4 Hz, 2H), 8.19–8.30 (m, 3H), 12.72 (br s, 1H) |

TABLE 5-continued

| Example No. | Compound No. | R² | R⁶ | * | ¹H-NMR (DMSO-d₆) |
|---|---|---|---|---|---|
| 38 | A-38 | HOOC—CH₂— | Cl—C₆H₄— | R | 2.46 (dd, J=6.9, 16.2 Hz, 1H), 2.63 (dd, J=6.3, 16.5 Hz, 1H), 4.13 (m, 1H), 7.60 (d, J=8.7 Hz, 2H), 7.93 (d, J=8.7 Hz, 2H), 7.95 (d, J=8.7 Hz, 2H), 7.99 (s, 1H), 8.42 (br s, 1H), 12.63 (br s, 2H) |
| 39 | A-39 | HOOC—CH₂— | Cl—C₆H₄— | S | 2.40–2.65 (m, 2H), 4.H (m, 1H), 7.61 (d, J=8.4 Hz, 2H), 7.95 (dd, J=8.4 Hz, 4H), 8.00 (s, 1H), 8.25 (d, J=8.4 Hz, 2H), 8.43 (m, 1H), 12.51 (br s, 2H) |
| 40 | A-40 | HOOC—CH₂— | F—C₆H₄— | S | 2.40–2.70 (m, 2H), 4.15 (m, 1H), 7.39 (t, J=8.7 Hz, 2H), 7.90–8.00 (m, 4H), 7.96 (s, 1H), 8.24 (d, J=8.4 Hz, 2H), 8.42 (br s, 1H), 12.50 (br s, 2H) |

TABLE 6

| Example No. | Compound No. | R² | R⁶ | * | ¹H-NMR (DMSO-d₆) |
|---|---|---|---|---|---|
| 41 | A-41 | HOOC—CH₂— | MeO—C₆H₄— | R | 2.47 (m, 1H), 2.63 (dd, J=6.6, 16.8 Hz, 1H), 3.83 (s, 3H), 4.12 (t, J=6.6 Hz, 1H), 7.09 (d, J=9.0 Hz, 2H), 7.79 (s, 1H), 7.82 (d, J=8.7 Hz, 2H), 7.93 (d, J=8.7 Hz, 2H), 8.22 (d, J=8.4 Hz, 2H), 8.40 (br s, 1H), 12.50 (br s, 2H) |
| 42 | A-42 | HOOC—CH₂— | MeO—C₆H₄— | S | 2.40–2.75 (m, 2H), 3.82 (s, 3H), 4.07 (m, 1H), 7.08 (d, J=8.7 Hz, 2H), 7.78 (s, 1H), 7.82 (d, J=8.7Hz, 2H), 7.92 (d, J=8.7 Hz, 2H), 8.22 (d, J=8.7 Hz, 2H), 8.40 (br s, 1H), 12.50 (br s, 2H) |
| 43 | A-43 | HOOC—(CH₂)₂— | Cl—C₆H₄— | R | 1.69 (m, 1H), 1.88 (m, 1H), 2.23 (t, J=7.2 Hz, 2H), 3.83 (m, 1H), 7.58–7.64 (m, 2H), 7.90–7.96 (m, 4H), 8.00 (s, 1H), 8.23–8.29 (m, 2H), 8.37 (br s, 1H), 12.42 (br s, 2H) |
| 44 | A-44 | HOOC—(CH₂)₂— | Cl—C₆H₄— | S | 1.69 (m, 1H), 1.88 (m, 1H), 2.23 (t, J=7.2 Hz, 2H), 3.83 (m, 1H), 7.58–7.63 (m, 2H), 7.89–7.95 (m, 4H), 7.99 (s, 1H), 8.23–8.29 (m, 2H), 8.36 (br s, 1H), 12.42 (br s, 2H) |
| 45 | A-45 | Ph | Cl—C₆H₄— | R | 4.97 (d, J=9.0 Hz, 1H), 7.19–7.33 (m, 5H), 7.57–7.63 (m, 2H), 7.85–7.95 (m, 4H), 7.98 (s, 1H), 8.14–8.19 (m, 2H7), 8.94 (d, J=9.3 Hz, 1H), 13.02 (br s, 1H) |
| 46 | A-46 | Me | naphthalen-2-yl | R | 1.21 (d, J=7.5 Hz, 3H), 3.87 (m, 1H), 7.54–7.65 (m, 2H), 7.95–8.09 (m, 7H), 8.29–8.39 (m, 3H), 7.94 (s, 1H), 7.96 (d, J=8.1 Hz, 2H7), 8.47 (s, 1H), 12.67 (br s, 1H) |
| 47 | A-47 | Me | naphthalen-2-yl | S | 1.21 (d, J=7.5 Hz, 3H), 3.87 (m, 1H), 7.54–7.65 (m, 2H), 7.95–8.09 (m, 7H), 8.29–8.41 (m, 3H), 7.94 (s, 1H), 7.96 (d, J=8.1 Hz, 2H), 8.47 (s, 1H), 12.68 (br s, 1H) |
| 48 | A-48 | Bn | naphthalen-2-yl | R | 2.76 (dd, J=9.3, 13.5 Hz, 1H), 2.99 (dd, J=5.1, 13.5 Hz, 1H), 3.97 (dt, J=5.7, 9.0 Hz, 1H), 7.11–7.26 (m, 5H), 7.54–7.65 (m, 2H), 7.76 (d, J=8.7 Hz, 2H), 7.98 (dd, J=2.1, 8.4 Hz, 1H), 8.01–8.10 (m, 4H), 8.18 (d, J=8.7 Hz, 2H), 8.44–8.53 (m, 2H), 12.80 (br s, 1H) |

TABLE 7
| Example No. | Compound No. | R² | R⁶ | * | ¹H-NMR (DMSO-d₆) |
|---|---|---|---|---|---|
| 49 | A-49 | Bn | naphthalen-2-yl | S | 2.76 (dd, J=9.3, 13.5 Hz, 1H), 2.99 (dd, J=5.1, 13.5 Hz, 1H), 3.97 (dt, J=5.1, 8.7 Hz, 1H), 7.11–7.26 (m, 5H), 7.54–7.65 (m, 2H), 7.76 (d, J=8.7 Hz, 2H), 7.98 (dd, J=2.4, 8.4 Hz, 1H), 8.01–8.10 (m, 4H), 8.19 (d, J=8.7 Hz, 2H), 8.47 (s, 1H), 8.49 d, J=8.7 Hz, 1H, 12.79 (br s, 1H) |
| 50 | A-50 | i-Pr | naphthalen-2-yl | R | 0.82 (d, J=6.6 Hz, 3H), 0.85 (d, J=6.9 Hz, 3H), 1.98 (m, 1H), 3.59 (dd, J=6.0, 9.3 Hz, 1H), 7.54–7.64 (m, 2H), 7.94–8.00 (m, 3H) 8.01–8.09 (m, 4H), 8.23 (d, J=9.3 Hz, 1H), 8.31 (d, J=8.7 Hz, 2H), 8.47 (s, 1H), 12.61 (br s, 1H) |
| 51 | A-51 | i-Pr | naphthalen-2-yl | S | 0.82 (d, J=6.9 Hz, 3H), 0.85 (d, J=6.9 Hz, 3H), 1.98 (m, 1H), 3.59 (dd, J=6.3, 9.3 Hz, 1H), 7.54–7.64 (m, 2H), 7.94–8.00 (m, 3H), 8.01–8.09 (m, 4H), 8.23 (d, J=9.3 Hz, 1H), 8.28–8.33 (m, 2H), 8.47 (s, 1H), 12.61 (br s, 1H) |
Example 52
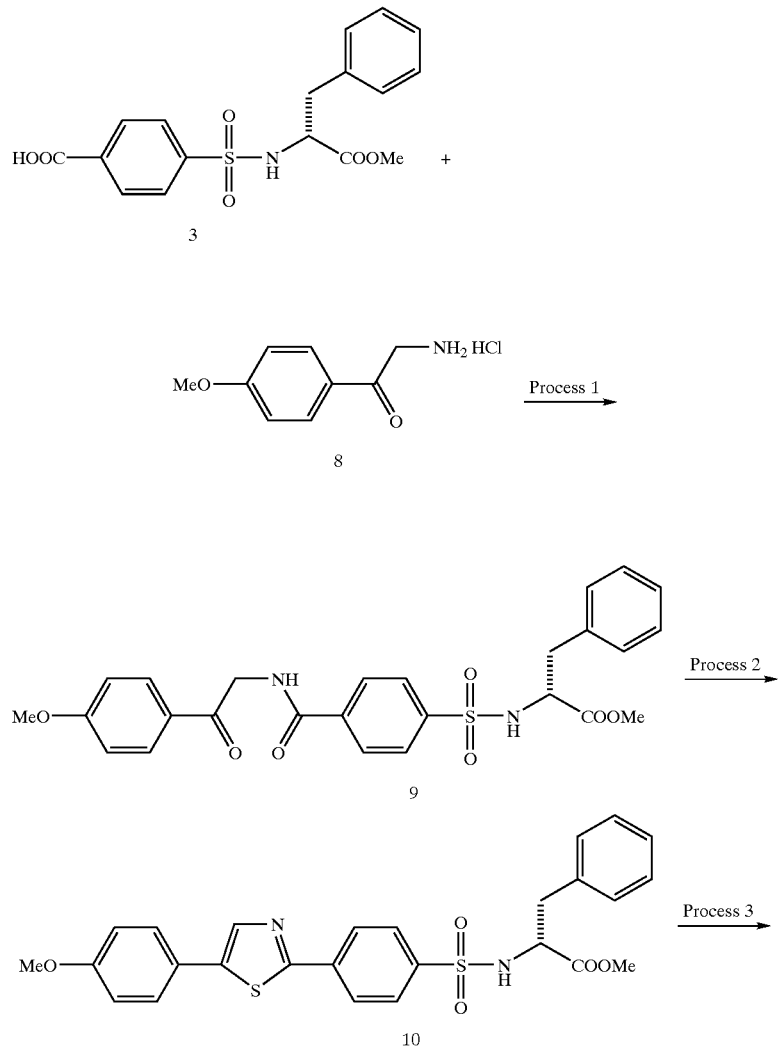

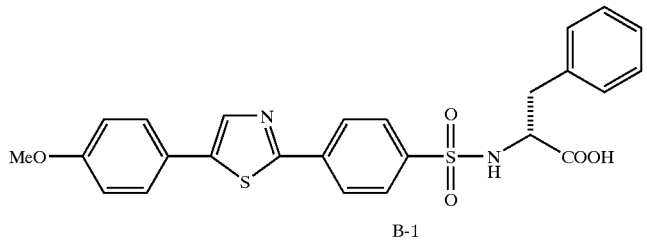

B-1

(Process 1)

Oxalyl chloride (0.31 ml, 3.6 mmol) was added to a suspension of compound (3) (1.09 g, 3 mmol) and dimethylformamide (0.05 ml) in dichloromethane (10 ml) with cooling in ice. The mixture was stirred at a room temperature for 1 h and concentrated under a reduced pressure. Pyridine (0.85 ml, 10.5 mmol) was added to a suspension of the crude acid chloride obtained above and 2-amino-4'-methoxyacetophenone hydrochloric acid salt (8) in dichloromethane (10 ml) with cooling in ice. The mixture was stirred at a room temperature 24 h, poured to ice-2 mol/L hydrochloric acid and extracted with ethyl acetate. The organic phase was washed with saturated aqueous sodium hydrogencarbonate solution and brine successively, dried over anhydrous sodium sulfate and concentrated under a reduced pressure. The residue was crystallized from tetrahydrofuran/hexane to give a desired product (9, 931 mg, yield 60.8%) with a melting point of 180–182 °C.

IR (KBr, ν max cm$^{-1}$) 3361, 3286, 1739, 1683, 1637, 1600, 1521, 1344, 1257, 1232, 1170, 1095 $^1$H NMR (DMSO-d$_6$, δ ppm): 2.78 (dd, J=9.0, 13.8 Hz, 1H), 2.95 (dd, J=6.0, 13.8 Hz, 1H), 3.33 (s, 3H), 3.86 (s, 3H), 4.03 (dt, J=6.0, 8.7 Hz, 1H), 4.76 (d, J=5.7 Hz, 2H), 7.09 (d, J=8.7 Hz, 2H), 7.09–7.25 (m, 5H), 7.67 (d, J=8.4 Hz, 2H), 7.94 (d, J=8.4 Hz, 2H), 8.04 (d, J=8.7 Hz, 2H), 8.66 (d, J=8.7 Hz, 1H), 8.97 (t, J=5.7 Hz, 1H) [α]$_{436-11.2±1.0}$ (c=0.502, DMSO, 24° C.) Elemental analysis (C$_{26}$H$_{26}$N$_2$O$_7$S.0.3H$_2$O) Calcd.: C, 60.52; H, 5.20; N, 5.43; S, 6.21. Found: C, 60.52; H, 5.04; N, 5.80; S, 6.13.

(Process 2)

A solution of compound (9) (445 mg, 0.872 mmol) and Lawesson's reagent (282 mg, 0.698 mmol) in tetrahydrofuran (6 ml) was stirred at 70° C. at 2 h, the reaction mixture was poured to ice-2 mol/L hydrochloric acid and extracted with ethyl acetate. The organic phase was washed with saturated aqueous sodium hydrogencarbonate solution and brine successively, dried over anhydrous sodium sulfate and concentrated under a reduced pressure. The residue was chromatographed on silica gel, chloroform/ethyl acetate=4/1 and crystallized from acetone/hexane to give a desired product (10, 386 mg, yield 87.0%) with a melting point of 185–186° C.

IR (KBr, ν max cm$^{-1}$) 3087, 1745, 1486, 1430, 1342, 1253, 1182, 1162, 1108, 1089, 829 $^1$H NMR (CDCl$_3$, δ ppm): 3.02 and 3.09 (dABq, J=6.0, 13.8 Hz, 2H), 3.53 (s, 3H), 3.86 (s, 3H), 4.25 (dt, J=9.3, 6.0 Hz, 1H), 5.13 (d, J=9.3 Hz, 1H), 6.93–7.00 (m, 2H), 7.04–7.12 (m, 2H), 7.21–7.29 (m, 3H), 7.51–7.58 (m, 2H), 7.76–7.83 (m, 2H), 7.97 (s, 1H), 7.97–8.03 (m, 2H) [α]$_D$–9.8±1.0 (c=0.511, DMSO, 24° C.) Elemental analysis (C$_{26}$H$_{24}$N$_2$O$_5$S$_2$.) Calcd.: C, 61.40; H, 4.76; N, 5.51; S, 12.61. Found: C, 61.30; H, 4.53; N, 5.53; S, 12.41.

(Process 3)

1 Mol/L aqueous sodium hydroxide solution (2.0 ml) was added to a solution of compound (10) (340 mg, 0.668 mmol) in dimethylsulfoxide (8 ml) at a room temperature and the mixture was stirred for 5 h. The obtained sodium salt was collected by filtration, poured to ice-2 mol/L hydrochloric acid and extracted with ethyl acetate. The organic phase was washed with brine, dried over anhydrous sodium sulfate and concentrated under a reduced pressure. The residue was crystallized from acetone/hexane to give a desired product (B-1) (300 mg, yield 90.8%) with a melting point of 222–223° C.

IR (KBr, ν max cm$^{-1}$) 3448, 3259, 2543, 1724, 1702, 1606, 1488, 1430, 1348, 1278, 1251, 1168, 1145, 1095, 835 $^1$H NMR (DMSO-d$_6$, δ ppm): 2.75 (dd, J=9.3, 13.5 Hz, 1H), 2.97 (dd, J=5.4, 13.5 Hz, 1H), 3.83 (s, 3H), 3.94 (dt, J=5.4, 9.0 Hz, 1H), 7.10 (d, J=9.0 Hz, 2H), 7.12–7.24 (m, 5H), 7.71 (d, J=8.4 Hz, 2H), 7.78 (s, 1H), 7.82 (d, J=9.0 Hz, 2H), 8.09 (d, J=8.4 Hz, 2H), 8.47 (d, J=9.0 Hz, 1H), 12.76 (br s, 1H) [α]$_{436-24.4±1.3}$ (c=0.501, DMSO, 25° C.) Elemental analysis (C$_{25}$H$_{22}$N$_2$O$_5$S$_2$) Calcd.: C, 60.71; H, 4.48; N, 5.66; S, 12.97. Found: C, 60.73; H, 4.41; N, 5.83; S, 12.67.

The following compounds (B-2) to (B-54) were synthesized in a manner similar to Example 52. Their results were shown in Table 8 to Table 14.

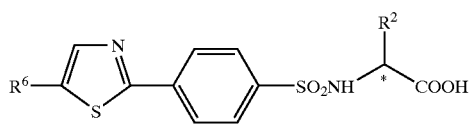

The mark * shows to be an optically active form unless R$^2$ is hydrogen atom and the absolute configuration was displayed in the table.

TABLE 8

| Example No. | Compound No. | R² | R⁶ | * | ¹H-NMR (DMSO-d₆) |
|---|---|---|---|---|---|
| 53 | B-2 | i-Pr | phenyl | R | 0.82 (d, J=6.6 Hz, 3H), 0.85 (d, J=6.9 Hz, 3H), 1.97 (m, 1H), 3.57 (dd, J=6.0, 8.7 Hz, 1H), 7.42 (m, 1H), 7.46–7.54 (m, 2H), 7.77 (d, J=8.7 Hz, 2H), 7.90 (d, J=8.4 Hz, 2H), 8.13 (d, J=8.4 Hz, 2H), 8.19 (d, J=8.7 Hz, 1H), 8.43 (s, 1H), 12.63 (br s, 1H) |
| 54 | B-3 | i-Pr | phenyl | S | 0.82 (d, J=6.6 Hz, 3H), 0.85 (d, J=7.2 Hz, 3H), 1.97 (m, 1H), 3.58 (dd, J=6.0, 9.3 Hz, 1H), 7.42 (m, 1H), 7.46–7.54 (m, 2H), 7.88–7.93 (m, 2H), 8.10–8.27 (m, 2H), 8.19 (d, J=9.3 Hz, 1H), 8.43 (s, 1H), 12.63 (br s, 1H) |
| 55 | B-4 | i-Pr | 4-Cl-phenyl | R | 0.82 (d, J=6.7 Hz, 3H), 0.85 (d, J=6.7 Hz, 3H), 1.97 (m, 1H), 3.58 (m, 1H), 7.56 (d, J=8.5 Hz, 2H), 7.79 (d, J=8.6 Hz, 2H), 7.91 (d, J=8.5 Hz, 2H), 8.13 (d, J=8.5 Hz, 2H), 8.20 (d, J=8.2 Hz, 1H), 8.46 (s, 1H) |
| 56 | B-5 | i-Pr | 4-Cl-phenyl | S | 0.82 (d, J=6.7 Hz, 3H), 0.85 (d, J=6.7 Hz, 3H), 1.97 (m, 1H), 3.57 (m, 1H), 7.56 (d, J=8.5 Hz, 2H), 7.79 (d, J=8.5 Hz, 2H), 7.91 (d, J=8.5 Hz, 2H), 8.13 (d, J=8.5 Hz, 2H), 8.20 (d, J=9.5 Hz, 1H), 8.46 (s, 1H) |
| 57 | B-6 | i-Pr | 4-MeO-phenyl | R | 0.82 (d, J=6.7 Hz, 3H), 0.85 (d, J=6.7 Hz, 3H), 1.96 (m, 1H), 3.57 (dd, J=6.1, 8.2 Hz, 1H), 3.82 (s, 3H), 7.06 (d, J=8.5 Hz, 2H), 7.69 (d, J=8.9 Hz, 2H), 7.89 (d, J=8.5 Hz, 2H), 8.11 (d, J=8.5 Hz, 2H), 8.17 (d, J=9.2 Hz, 1H), 8.30 (s, 1H) |
| 58 | B-7 | i-Pr | 4-MeO-phenyl | S | 0.81 (d, J=6.6 Hz, 3H), 0.85 (d, J=6.9 Hz, 3H), 1.96 (m, 1H), 3.57 (m, 1H), 3.82 (s, 3H), 7.06 (d, J=9.0 Hz, 2H), 7.70 (d, J=9.0 Hz, 2H), 7.89 (d, J=8.4 Hz, 2H), 8.11 (d, J=8.7 Hz, 2H), 8.19 (d, J=9.3 Hz, 1H), 8.30 (s, 1H), 12.64 (br s, 1H) |
| 59 | B-8 | i-Pr | 4-F-phenyl | R | 0.82 (d, J=6.9 Hz, 3H), 0.85 (d, J=6.9 Hz, 3H), 1.97 (m, 1H), 3.58 (dd, J=6.0, 9.0 Hz, 1H), 7.35 (t, J=8.7 Hz, 2H), 7.78–7.86 (m, 2H), 7.88–7.93 (m, 2H), 8.10–8.15 (m, 2H), 8.21 (d, J=9.0 Hz, 1H), 8.40 (s, 1H), 12.64 (br s, 1H) |

TABLE 9

| Example No. | Compound No. | R² | R⁶ | * | ¹H-NMR (DMSO-d₆) |
|---|---|---|---|---|---|
| 60 | B-9 | i-Pr | 4-F-phenyl | S | 0.81 (d, J=6.9 Hz, 3H), 0.85 (d, J=6.9 Hz, 3H), 1.96 (m, 1H), 3.57 (dd, J=6.0, 9.3 Hz, 1H), 7.31–7.40 (m, 2H), 7.78–7.85 (m, 2H), 7.88–7.93 (m, 2H), 8.10–8.15 (m, 2H), 8.20 (d, J=9.3 Hz, 1H), 8.39 (s, 1H), 12.62 (br s, 1H) |
| 61 | B-10 | i-Pr | 4-Br-phenyl | R | 0.81 (d, J=6.9 Hz, 3H), 0.85 (d, J=6.9 Hz, 3H), 1.97 (m, 1H), 3.57 (m, 1H), 7.66–7.76 (m, 4H), 7.90 (d, J=8.4 Hz, 2H), 8.13 (d, J=8.4 Hz, 2H), 8.16 (d, J=9.0 Hz, 1H), 8.47 (s, 1H), 12.62 (br s, 1H) |

TABLE 9-continued

| Example No. | Compound No. | R² | R⁶ | * | ¹H-NMR (DMSO-d₆) |
|---|---|---|---|---|---|
| 62 | B-11 | Bn | phenyl | R | 2.75 (dd, J=9.6, 13.5 Hz, 1H), 2.98 (dd, J=5.7, 13.5 Hz, 1H), 3.94 (m, 1H), 7.10–7.24 (m, 5H), 7.42 (m, 1H), 7.46–7.54 (m, 2H), 7.67 (d, J=8.4 Hz, 2H), 7.77 (d, J=8.4 Hz, 2H), 7.99 (d, J=8.4 Hz, 2H), 8.43 (s, 1H), 8.45 (d, J=8.1 Hz, 1H), 12.80 (br s, 1H) |
| 63 | B-12 | Bn | phenyl | S | 2.74 (dd, J=9.3, 13.5 Hz, 1H), 2.98 (dd, J=5.1, 13.5 Hz, 1H), 3.93 (dt, J=5.1, 8.7 Hz, 1H), 7.10–7.24 (m, 5H), 7.42 (m, 1H), 7.46–7.54 (m, 2H), 7.64–7.69 (m, 2H), 7.77 (d, J=8.1 Hz, 2H), 7.96–8.01 (m, 2H), 8.43 (s, 1H), 8.46 (d, J=8.7 Hz, 1H), 12.80 (br s, 1H) |
| 64 | B-13 | Bn | 4-Cl-phenyl | R | 2.74 (dd, J=9.6, 13.4 Hz, 1H), 2.98 (dd, J=5.4, 13.9 Hz, 1H), 3.94 (d, J=5.5 Hz, 1H), 7.16–7.18 (m, 5H), 7.57 (d, J=8.2 Hz, 2H), 7.67 (d, J=8.2 Hz, 2H), 7.80 (d, J=8.2 Hz, 2H), 7.98 (d, J=8.0 Hz, 2H), 8.46 (s, 1H), 8.48 (d, J=7.7 Hz, 1H) |
| 65 | B-14 | Bn | 4-Cl-phenyl | S | 2.74 (dd, J=9.6, 13.8 Hz, 1H), 2.98 (dd, J=5.4, 13.8 Hz, 1H), 3.93 (m, 1H), 7.10–7.22 (m, 5H), 7.53–7.60 (m, 2H), 7.66 (d, J=8.7 Hz, 2H), 7.77–7.83 (m, 2H), 7.98 (d, J=8.7 Hz, 2H), 8.46 (s, 1H), 8.47 (d, J=8.4 Hz, 1H), 12.81 (br s, 1H) |
| 66 | B-15 | Bn | 4-MeO-phenyl | R | 2.74 (dd, J=9.6, 13.8 Hz, 1H), 2.97 (dd, J=5.7, 13.8 Hz, 1H), 3.82 (s, 3H), 3.93 (dt, J=5.4, 8.7 Hz, 1H), 7.06 (d, J=9.0 Hz, 2H), 7.10–7.23 (m, 5H), 7.65 (d, J=8.7 Hz, 2H), 7.70 (d, J=9.0 Hz, 2H), 7.96 (d, J=8.7 Hz, 2H), 8.30 (s, 1H), 8.44 (d, J=8.7 Hz, 1H), 12.80 (br s, 1H) |

TABLE 10

| Example No. | Compound No. | R² | R⁶ | * | ¹H-NMR (DMSO-d₆) |
|---|---|---|---|---|---|
| 67 | B-16 | Bn | 4-MeO-phenyl | S | 2.73 (dd, J=9.6, 13.8 Hz, 1H), 2.96 (dd, J=5.4, 13.5 Hz, 1H), 3.81 (s, 3H), 3.92 (m, 1H), 7.05 (d, J=8.7 Hz, 2H), 7.10–7.24 (m, 5H), 7.64 (d, J=8.4 Hz, 2H), 7.69 (d, J=8.4 Hz, 2H), 7.95 (d, J=8.1 Hz, 2H), 8.29 (a, 1H), 8.44 (d, J=9.0 Hz, 1H) 12.81 (br s, 1H) |
| 68 | B-17 | Bn | 4-F-phenyl | R | 2.72 (dd, J=9.3, 13.5 Hz, 1H), 2.97 (dd, J=5.4, 13.5 Hz, 1H), 3.93 (m, 1H), 7.10–7.22 (m, 5H), 7.31–7.40 (m, 2H), 7.66 (d, J=8.4 Hz, 2H), 7.78–7.86 (m, 2H), 7.97 (d, J=8.4 Hz, 2H), 8.39 (a, 1H), 8.46 (d, J=9.0 Hz, 1H), 12.82 (br s, 1H) |
| 69 | B-18 | Bn | 4-F-phenyl | S | 2.74 (dd, J=9.9, 13,8 Hz, 1H), 2.98 (dd, J=5.1, 13.8 Hz, 1H), 3.93 (m, 1H), 7.10–7.22 (m, 5H), 7.36 (t J=8.7 Hz, 2H), 7.66 (d, J=8.4 Hz, 2H), 7.80–7.85 (m, 2H), 7.97 (d, J=8.4 Hz, 2H), 8.40 (s, 1H), 8.47 (d, J=8.7 Hz, 1H), 12.80 (br s, 1H) |
| 70 | B-19 | Bn | 4-Br-phenyl | R | 2.74 (dd, J=9.6, 13.8 Hz, 1H), 2.97 (dd, J=5.7, 13.8 Hz, 1H), 3.94 (m, 1H), 7.10–7.22 (m, 5H), 7.62–7.78 (m, 6H), 7.98 (d, J=8.7 Hz, 2H), 8.46 (d, J=7.5 Hz, 2H), 12.80 (br s, 1H) |

TABLE 10-continued

| Example No. | Compound No. | R² | R⁶ | * | ¹H-NMR (DMSO-d₆) |
|---|---|---|---|---|---|
| 71 | B-20 | Bn | 4-Br-C₆H₄- | S | 2.74 (dd, J=9.3, 13,5 Hz, 1H), 2.97 (dd, J=5.1, 13.5 Hz, 1H), 3.92 (m, 1H), 7.30–7.42 (m, 5H), 7.64–7.75 (m, 6H), 7.98 (d, J=8.4 Hz, 2H), 8.47 (s, 1H), 8.47 (d, J=9.6 Hz, 1H), 12.80 (br s, 1H) |
| 72 | B-21 | Me | C₆H₅- | R | 1.20 (d, J=7.5 Hz, 3H), 3.84 (m, 1H), 7.42 (m, 1H), 7.46–7.54 (m, 2H), 7.77 (d, J=8.1 Hz, 2H), 7.92 (d, J=8.4 Hz, 2H), 8.15 (d, J=8.4 Hz, 2H), 8.32 (d, J=8.4 Hz, 1H), 8.43 (s, 1H), 12.68 (br s, 1H) |
| 73 | B-22 | Me | C₆H₅- | S | 1.20 (d, J=7.5 Hz, 3H), 3.84 (m, 1H), 7.42 (m, 1H), 7.46–7.54 (m, 2H), 7.77 (d, J=7.8 Hz, 2H), 7.89–7.94 (m, 2H), 8.12–8.18 (m, 2H), 8.32 (d, J=9.0 Hz, 1H), 8.43 (a, 1H), 12.68 (br s, 1H) |
| 74 | B-23 | Me | 4-MeO-C₆H₄- | R | 1.19 (d, J=7.1 Hz, 3H), 3.82 (s, 3H), 3.82–3.86 (m, 1H), 7.06 (d, J=8.8 Hz, 2H), 7.69 (d, J=8.8 Hz, 2H), 7.90 (d, J=8.5 Hz, 2H), 8.12 (d, J=8.2 Hz, 2H), 8.30 (m, 2H) |

TABLE 11

| Example No. | Compound No. | R² | R⁶ | * | ¹H—NMR (DMSO-d₆) |
|---|---|---|---|---|---|
| 75 | B-24 | Me | 4-MeO-C₆H₄- | S | 1.20(d, J=7.2Hz, 3H), 3.82(s, 3H), 3.83 (m, 1H), 7.06(d, J=8.7Hz, 2H), 7.70(d, J=8.7Hz, 2H), 7.90(d, J=8.4Hz, 2H), 8.12(d, J=8.4Hz, 2H), 8.30(s, 1H), 8.31 (br s, 1H), 12.61(br s, 1H) |
| 76 | B-25 | Me | 4-Cl-C₆H₄- | R | 1.20(d, J=7.5Hz, 3H), 3.84(m, 1H), 7.53–7.59(m, 2H), 7.77–7.82(m, 2H), 7.89–7.96(m, 2H), 8.12–8.17(m, 2H), 8.31(d, J=7.5Hz, 1H), 8.46(s, 1H), 12.60(br s, 1H) |
| 77 | B-26 | Me | 4-Cl-C₆H₄- | S | 1.19(d, J=7.5Hz, 3H), 3.83(m, 1H), 7.53–7.60(m, 2H), 7.77–7.83(m, 2H), 7.89–7.95(m, 2H), 8.11–8.18(m, 2H), 8.32(d, J=6.6Hz, 1H), 8.46(s, 1H), 12.65(br s, 1H) |
| 78 | B-27 | Me | 4-F-C₆H₄- | R | 1.19(d, J=7.2Hz, 3H), 3.84(m, 1H), 7.31–7.40(m, 2H), 7.79–7.86(m, 2H), 7.89–7.95(m, 2H), 8.12–8.17(m, 2H), 8.35(d, J=7.5Hz, 1H), 8.41(s, 1H), 12.71(br s, 1H) |
| 79 | B-28 | Me | 4-F-C₆H₄- | S | 1.19(d, J=7.2Hz, 3H), 3.84(m, 1H), 7.31–7.40(m, 2H), 7.78–7.86(m, 2H), 7.89–7.94(m, 2H), 8.11–8.17(m, 2H), 8.33(d, J=8.7Hz, 1H), 8.40(s, 1H), 12.65(br s, 1H) |
| 80 | B-29 | Me | 4-Br-C₆H₄- | R | 1.19(d, J=7.2Hz, 3H), 3.83(m, 1H), 7.67–7.75(m, 4H), 7.89–7.95(m, 2H), 8.12–8.17(m, 2H), 8.30(br s, 1H), 8.47 (s, 1H), 12.71(br s, 1H) |
| 81 | B-30 | Me | 4-Br-C₆H₄- | S | 1.19(d, J=7.2Hz, 3H), 3.84 ((m, 1H), 7.68–7.75(m, 4H), 7.89–7.93(m, 2H), 8.13–8.16(m, 2H), 8.33(d, J=8.4Hz, 1H), 8.47(s, 1H), 12.70(br s, 1H) |

TABLE 11-continued

| Example No. | Compound No. | R² | R⁶ | * | ¹H—NMR (DMSO-d₆) |
|---|---|---|---|---|---|
| 82 | B-31 | i-Bu | 4-Cl-C₆H₄— | R | 0.73(d, J=6.6Hz, 3H), 0.83(d, J=6.6Hz, 3H), 1.33–1.50(m, 2H), 1.61 (m, 1H), 3.71(m, 1H), 7.56(d, J=8.7Hz, 2H), 7.79(d, J=8.7Hz, 2H), 7.89 (d, J=8.4Hz, 2H), 8.14(d, J=8.4Hz, 2H), 8.32(d, J=7.8Hz, 1H), 8.46(s, 1H), 12.61(br s, 1H) |

TABLE 12

| Example No. | Compound No. | R² | R⁶ | * | ¹H—NMR (DMSO-d₆) |
|---|---|---|---|---|---|
| 83 | B-32 | i-Bu | 4-Cl-C₆H₄— | S | 0.73(d, J=6.3Hz, 3H), 0.83(d, J=6.3Hz, 3H), 1.38–1.46(m, 2H), 1.61(m, 1H), 3.71(m, 1H), 7.56(d, J=8.4Hz, 2H), 7.80(d, J=8.7Hz, 2H), 7.89(d, J=8.7Hz, 2H), 8.14(d, J=8.4Hz, 2H), 1H) |
| 84 | B-33 | i-Bu | 4-F-C₆H₄— | S | 0.73(d, J=6.3Hz, 3H), 0.83(d, J=6.6Hz, 3H), 1.38–1.45(m, 2H), 1.60(m, 1H), 3.70(m, 1H), 7.35(t, J=9.0Hz, 2H), 7.82(dd, J=5.4, 9.0Hz, 2H), 7.89 (d, J=8.7Hz, 2H), 8.13(d, J=8.4Hz, 2H), 8.32(d, J=7.5Hz, 1H), 8.40(s, 1H), 12.68(br s, 1H) |
| 85 | B-34 | i-Bu | 4-MeO-C₆H₄— | R | 0.73(d, J=6.6Hz, 3H), 0.83(d, J=6.3Hz, 3H), 1.33–1.50(m, 2H), 1.61(m, 1H), 3.71(m, 1H), 3.82(s, 3H), 7.03–7.09(m, 2H), 7.66–7.72(m, 2H), 7.86–7.91(m, 2H), 8.09–8.14(m, 2H), 8.29 (br s, 1H), 8.30(s, 1H), 12.65(br s, 1H) |
| 86 | B-35 | i-Bu | 4-MeO-C₆H₄— | S | 0.73(d, J=6.6Hz, 3H), 0.83(d, J=6.9Hz, 3H), 1.38–1.44(m, 2H), 1.61(m, 1H), 3.71(m, 1H), 3.82(s, 3H), 7.06(d, J=9.0Hz, 2H), 7.69(d, J=8.7Hz, 2H), 7.88(d, J=8.7Hz, 2H), 8.11(d, J=8.7Hz, 2H), 8.30(s, 2H), 12.60(br s, 1H) |
| 87 | B-36 | s-Bu | 4-MeO-C₆H₄— | S | 0.73–0.86(m, 6H), 1.12(m, 1H), 1.37 (m, 1H), 1.69(m, 1H), 3.60(m, 1H), 3.82(s, 3H), 7.06(d, J=9.0Hz, 2H), 7.70 (d, J=9.0Hz., 2H), 7.89(d, J=8.4Hz, 2H), 8.11(d, J=8.7Hz, 2H), 8.22(d, J=9.3Hz, 1H), 8.31(s, 1H), 12.65(br s, 1H) |
| 88 | B-37 | s-Bu | 4-Br-C₆H₄— | S | 0.75–0.83(m, 6H), 1.12(m, 1H), 1.37 (m, 1H), 1.69(m, 1H), 3.60(m, 1H), 7.06(d, J=9.0Hz, 2H), 7.71(d, J=9.0Hz., 2H), 7.90(d, J=8.4Hz, 2H), 8.13(d, J=8.7Hz, 2H), 8.22(d, J=9.3Hz, 1H), 8.47(s, 1H), 12.65(br s, 1H) |
| 89 | B-38 | HOOC—CH₂— | 4-Cl-C₆H₄— | R | 2.47(dd, J=6.9, 16.2Hz, 1H), 2.64(dd, J=6.5, 16.2Hz, 1H), 4.13(m, 1H), 7.57 (d, J=8.7Hz, 2H), 7.80(d, J=8.7Hz, 2H), 7.91(d, J=8.7Hz, 2H), 8.14(d, J=8.4Hz, 2H), 8.39(m, 1H), 8.46(s, 1H), 12.58(s, 2H) |

TABLE 13

| Example No. | Compound No. | R² | R⁶ | * | ¹H—NMR (DMSO-d₆) |
|---|---|---|---|---|---|
| 90 | B-39 | HOOC—CH₂— | Cl-C₆H₄- (4-Cl-phenyl) | S | 2.40–2.65(m, 2H), 4.15(m, 1H), 7.60(d, J=8.4Hz, 2H), 7.92(d, J=8.4Hz, 2H), 7.95(d, J=8.4Hz, 2H), 7.99(s, 1H), 8.25(d, J=8.4Hz, 2H) 8.42 (br s, 1H) 12.59 (br s, 2H) |
| 91 | B-40 | HOOC—CH₂— | MeO-C₆H₄- (4-MeO-phenyl) | R | 2.47(m, 1H), 2.64(dd, J=6.3, 16.5Hz, 1H), 3.82(s, 3H), 4.12(t, J=6.3Hz, 1H), 7.06(d, J=8.7Hz, 2H), 7.70(d, J=8.7Hz, 2H), 7.90(d, J=8.7Hz, 2H), 8.11(d, J=8.7Hz, 2H), 8.30(s, 1H), 8.37(br s, 1H), 12.60(br s, 1H) |
| 92 | B-41 | HOOC—CH₂— | MeO-C₆H₄- (4-MeO-phenyl) | S | 2.20–2.44(m, 2H), 3.87(m, 1H), 6.82(d, J=8.7Hz, 2H), 7.46(d, J=8.9Hz, 2H), 7.66(d, J=8.7Hz, 2H), 7.94(d, J=8.7Hz, 2H), 8.07(s, 1H), 8.10(br s, 1H) |
| 93 | B-42 | HOOC—CH₂— | F-C₆H₄- (4-F-phenyl) | S | 2.42–2.75(m, 2H), 4.16(m, 1H), 7.35(t, J=8.7Hz, 2H), 7.85(t, J=8.7Hz, 2H), 7.91(d, J=8.4Hz, 2H), 8.13(d, J=8.4Hz, 2H), 8.40(a, 1H), 8.41(br s, 1H), 12.50 (br s, 2H) |
| 94 | B-43 | HOOC—(CH₂)₂— | Cl-C₆H₄- (4-Cl-phenyl) | R | 1.68(m, 1H), 1.89(m, 1H), 2.24(t, J=6.9Hz, 2H), 3.83(m, 1H), 7.54–7.60(m, 2H), 7.77–7.83(m, 2H), 7.86–7.92(m, 2H), 8.11–8.17(m, 2H), 8.35(br s, 1H), 8.47(s, 1H), 12.43(br s, 2H) |
| 95 | B-44 | HOOC—(CH₂)₂— | Cl-C₆H₄- (4-Cl-phenyl) | S | 1.69(m, 1H), 1.89(m, 1H), 2.23(t, J=7.2Hz, 2H), 3.83(m, 1H), 7.53–7.60(m, 2H), 7.77–7.82(m, 2H), 7.89(d, J=8.4Hz, 2H), 8.13(d, J=8.4Hz, 2H), 8.34(br s, 1H), 8.46(s, 1H), 12.44(br s, 2H) |
| 96 | B-45 | CH₃S—CH₂CH₂— | C₆H₅- (phenyl) | R | 1.67–1.93(m, 2H), 1.94(s, 3H), 2.27–2.49(m, 2H), 3.91(m, 1H), 7.42(m, 1H), 7.46–7.54(m, 2H), 7.74–7.80(m, 2H), 7.90(d, J=8.4Hz, 2H), 8.15(d, J=8.4Hz, 2H), 8.37(d, J=8.1Hz, 1H), 8.43(s, 1H), 12.75(br s, 1H) |
| 97 | B-46 | CH₃S—CH₂CH₂— | Cl-C₆H₄- (4-Cl-phenyl) | R | 1.67–1.93(m, 2H), 1.94(s, 3H), 2.27–2.50(m, 2H), 3.91(m, 1H), 7.53–7.59(m, 2H), 7.76–7.82(m, 2H), 7.87–7.93(m, 2H), 8.12–8.17(m, 2H), 8.37(d, J=8.4Hz, 1H), 8.46(s, 1H), 12.79(br s, 1H) |

TABLE 14

| Example No. | Compound No. | R² | R⁶ | * | ¹H—NMR (DMSO-d₆) |
|---|---|---|---|---|---|
| 98 | B-47 | CH₃S—CH₂CH₂— | MeO-C₆H₄- (4-MeO-phenyl) | R | 1.65–1.95(m, 2H), 1.94(s, 3H), 2.26–2.50(m, 2H), 3.82(s, 3H), 3.91(m, 1H), 7.06(d, J=9.0Hz, 2H), 7.70(d, J=9.0Hz, 2H), 7.89(d, J=8.4Hz, 2H), 8.12(d, J=8.4Hz, 2H), 8.31(s, 1H), 8.36(d, J=9.0Hz, 1H), 12.79(br s, 1H) |
| 99 | B-48 | CH₃S—CH₂CH₂— | Br-C₆H₄- (4-Br-phenyl) | R | 1.65–1.95(m, 2H), 1.94(s, 3H), 2.25–2.50(m, 2H), 3.91(m, 1H), 7.67–7.76(m, 4H), 7.90(d, J=8.1Hz, 2H), 8.15(d, J=8.7Hz, 2H), 8.38(d, J=9.3Hz, 1H), 8.48(s, 1H), 12.79(br s, 1H) |
| 100 | B-49 | CH₃S—CH₂CH₂— | F-C₆H₄- (4-F-phenyl) | R | 1.66–1.93(m, 2H), 1.94(s, 3H), 2.28–2.48(m, 2H), 3.91(m, 1H), 7.78–7.85(m, 4H), 7.90(d, J=8.1Hz, 2H), 8.14(d, J=8.7Hz, 2H), 8.36(d, J=9.3Hz, 1H), 8.40(s, 1H), 12.69(br s, 1H) |

TABLE 14-continued

| Example No. | Compound No. | R² | R⁶ | * | ¹H—NMR (DMSO-d₆) |
|---|---|---|---|---|---|
| 101 | B-50 | CH₃S—CH₂CH₂— | Br-C₆H₄- | S | 1.65–1.96(m, 2H), 1.94(s, 3H), 2.25–2.48(m, 2H), 3.91(m, 1H), 7.67–7.76 (m, 4H), 7.90(d, J=8.1Hz, 2H), 8.16(d, J=8.7Hz, 2H), 8.38(d, J=9.3Hz, 1H), 8.48(s, 1H), 12.79(br s, 1H) |
| 102 | B-51 | (Indole-3-yl)methyl | Cl-C₆H₄- | R | 2.88(dd, J=8.1, 14.1Hz, 1H), 3.09(dd, J=5.7, 14.1Hz, 1H), 3.96(m, 1H), 6.84–7.02(m, 2H), 7.09(d, J=2.1Hz, 1H), 7.20(d, J=7.8Hz, 1H), 7.32(d, J=7.8Hz, 1H), 7.76–7.94(m, 4H), 7.50–7.65 (m, 4H), 8.43(d, J=9.0Hz, 1H), 8.46(s, 1H) |
| 103 | B-52 | H | Cl-C₆H₄- |   | 3.66(s, 2H), 7.57(d, J=8.1Hz, 2H), 7.80 (d, J=8.1Hz, 2H), 7.94(d, J=8.1Hz, 2H), 8.16(d, J=8.1Hz, 2H), 8.22(br s, 1H), 8.46(s, 1H) |
| 104 | B-53 | Me | naphthyl | R | 1.21(d, J=7.5Hz, 3H), 3.86(m, 1H), 7.53–7.63(m, 2H), 7.90–8.07(m, 6H), 8.18(d, J=8.1Hz, 2H), 8.31(d, J=1.2Hz, 1H), 8.33(d, J=8.7Hz, 1H), 8.57(s, 1H), 12.69(br s, 1H) |
| 105 | B-54 | Me | naphthyl | S | 1.21(d, J=7.5Hz, 3H), 3.86(m, 1H), 7.53–7.63(m, 2H), 7.91–8.07(m, 6H), 8.18(d, J=8.1Hz, 2H), 8.31(s, 1H), 8.33 (d, J=8.7Hz, 1H), 8.57(s, 1H), 12.69 (br s, 1H) |

Example 106

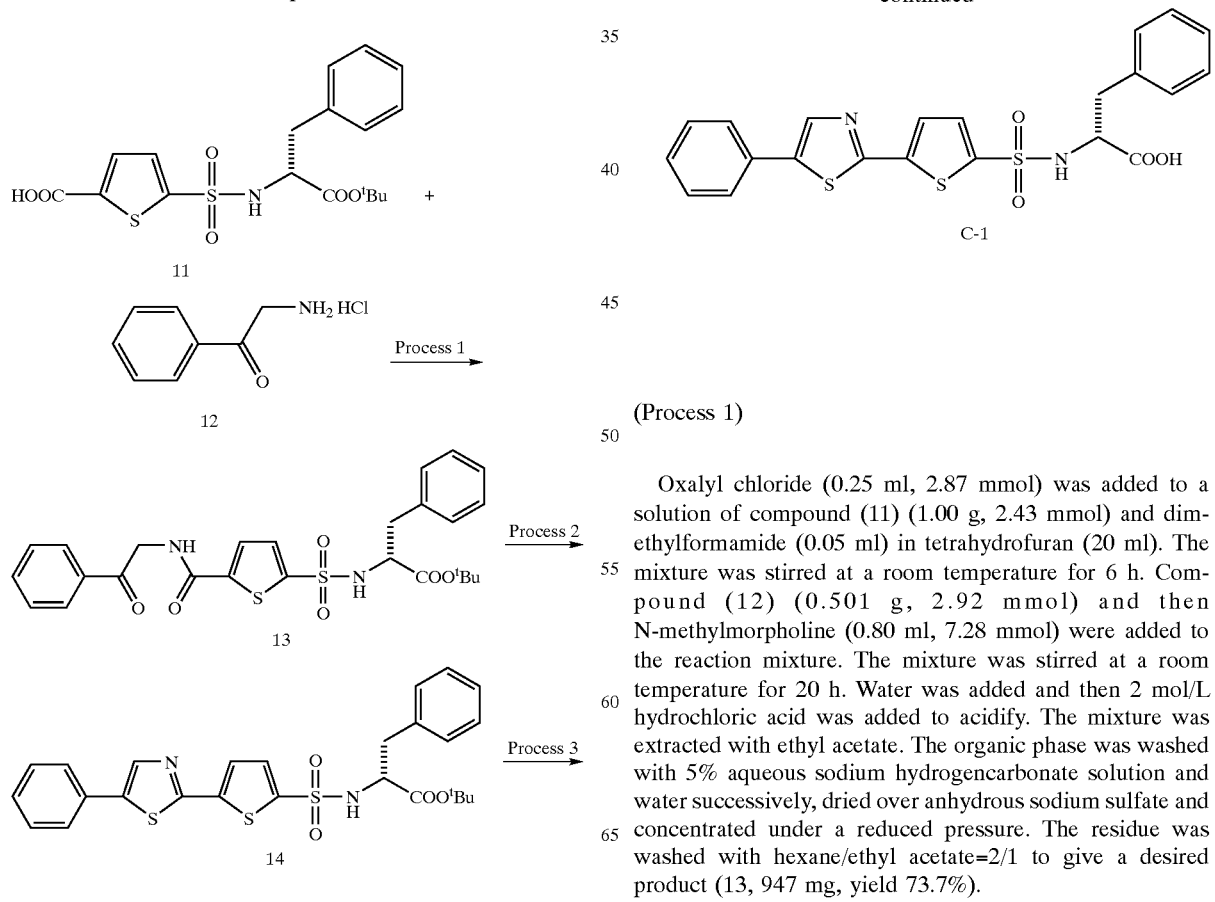

(Process 1)

Oxalyl chloride (0.25 ml, 2.87 mmol) was added to a solution of compound (11) (1.00 g, 2.43 mmol) and dimethylformamide (0.05 ml) in tetrahydrofuran (20 ml). The mixture was stirred at a room temperature for 6 h. Compound (12) (0.501 g, 2.92 mmol) and then N-methylmorpholine (0.80 ml, 7.28 mmol) were added to the reaction mixture. The mixture was stirred at a room temperature for 20 h. Water was added and then 2 mol/L hydrochloric acid was added to acidify. The mixture was extracted with ethyl acetate. The organic phase was washed with 5% aqueous sodium hydrogencarbonate solution and water successively, dried over anhydrous sodium sulfate and concentrated under a reduced pressure. The residue was washed with hexane/ethyl acetate=2/1 to give a desired product (13, 947 mg, yield 73.7%).

¹H NMR (CDCl₃, δ ppm): 1.30 (s, 9H), 3.08 (d, J=5.8 Hz, 2H), 4.23 (m, 1H), 4.93 (d, J=3.7 Hz, 2H), 5.33 (d, J=9.2 Hz, 1H), 7.15–7.28 (m, 6H), 7.46–7.57 (m, 4H), 7.68 (m, 1H), 8.02 (d, J=8.5 Hz, 1H)

(Process 2)

A solution of compound (13) (470 mg, 0.889 mmol) and Lawesson's reagent (360 mg, 0.890 mmol) in tetrahydrofuran (5 ml) was stirred at 70° C. for 4 h. Lawesson's reagent (180 mg, 0.445 mmol) was added to the mixture, which was stirred further 4 h. Water was added to the mixture, which was acidified with 2 mol/L hydrochloric acid and extracted with ethyl acetate. The organic phase was washed with 5% aqueous sodium hydrogencarbonate solution and water successively, dried over anhydrous sodium sulfate and concentrated under a reduced pressure. The residue was chromatographed on silica gel in chloroform/ethyl acetate=10/1 and crystallized from acetone/hexane to give a desired product (14, 337 mg, yield 71.9%) with a melting point of 163–165° C.

IR (KBr, ν max cm⁻¹) 3446, 3292, 2979, 1712, 1427, 1408, 1367, 1348, 1288, 1157, 1084, 1020, 897 ¹H NMR (CDCl₃, δ ppm): 1.27 (s, 9H), 3.08 (d, J=5.8 Hz, 2H), 4.24 (m, 1H), 5.28 (d, J=9.1 Hz, 1H), 7.16–7.30 (m, 6H), 7.36–7.47 (m, 4H), 7.58 (d, J=6.9 Hz, 2H), 7.97 (s, 1H) [α]$_{D-16.0\pm1.1}$ (c=0.506, DMSO, 27° C.)

(Process 3)

Trifluoroacetic acid (0.823 ml, 10.7 mmol) was added to a solution of compound (14) (281 mg, 0.534 mmol) in dichloromethane (7 ml). The mixture was stirred for 20 h and concentrated under a reduced pressure. Toluene was added to the residue and the mixture was concentrated under a reduced pressure again. The residue was crystallized from acetone/hexane to give a desired product (C-1, 204 mg, yield 81.1%) with a melting point of 233–234° C.

IR (KBr, ν max cm⁻¹) 3340, 3087, 1736, 1701, 1377, 1352, 1165, 1105, 1018, 812 ¹H NMR (DMSO-d₆, δ ppm): 2.76 (dd, J=9.9, 13.7 Hz, 1H), 3.01 (dd, J=4.7, 13.5 Hz, 1H), 4.00 (m, 1H), 7.13–7.18 (m, 5H), 7.31 (d, J=3.8 Hz, 1H), 7.39–7.55 (m, 4H), 7.74 (d, J=7.1 Hz, 2H), 8.33 (s, 1H), 8.76 (d, J=6.9 Hz, 1H) [α]$_D$-13.9±1.1 (c=0.504, DMSO, 27° C.)

The following compounds (C-2) were synthesized in a manner similar to Example 106. Their results were shown in Table 15.

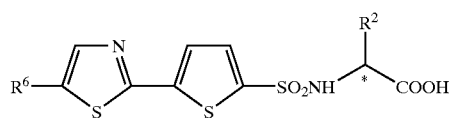

The mark * shows to be an optically active form and the absolute configuration was displayed in the table.

TABLE 15

| Example No. | Compound No. | R² | R⁶ | * | ¹H—NMR (DMSO-d₆) |
|---|---|---|---|---|---|
| 107 | C-2 | i-Pr | (phenyl) | R | 0.83(d, J=6.9Hz, 3H), 0.88(d, J=6.9Hz, 3H), 2.01(m, 1H), 3.65 (m, 1H), 7.39–7.52(m, 3H), 7.57(d, J=4.1Hz, 1H), 7.69(d, J=4.1Hz, 1H), 7.73(d, J=8.0Hz, 2H), 8.33(s, 1H), 8.52(s, 1H) |

The following compounds (D-1) to (D-15), (E-1) to (E-19), and (F-1) to (F-7) in Table 16 to Table 19 can be synthesized in a similar manner.

TABLE 16

| Compound No. | R² | R⁶ |
|---|---|---|
| D-1 | i-Pr | MeO—(C₆H₄)— |
| D-2 | HOOCCH₂— | (phenyl) |
| D-3 | (indol-3-yl)CH₂— | (phenyl) |
| D-4 | (indol-3-yl)CH₂— | MeO—(C₆H₄)— |
| D-5 | (indol-3-yl)CH₂— | F—(C₆H₄)— |
| D-6 | HO—(C₆H₄)— | (phenyl) |
| D-7 | HO—(C₆H₄)— | MeO—(C₆H₄)— |
| D-8 | HO—(C₆H₄)— | F—(C₆H₄)— |
| D-9 | MeSCH₂CH₂— | (phenyl) |

TABLE 16-continued
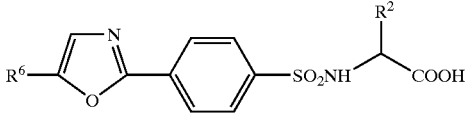
| Compound No. | R² | R⁶ |
|---|---|---|
| D-10 | MeSCH₂CH₂— | 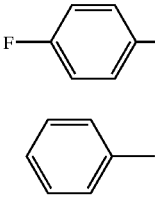 |
| D-11 | i-Bu | 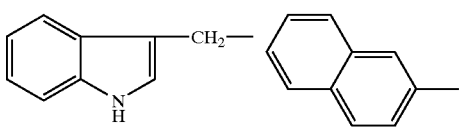 |
| D-12 | 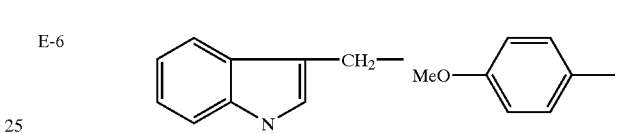 | 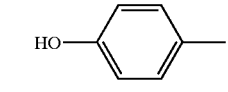 |
| D-13 | 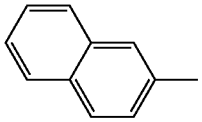 | 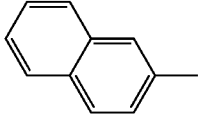 |
| D-14 | MeSCH₂CH₂— | 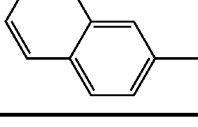 |
| D-15 | i-Bu | 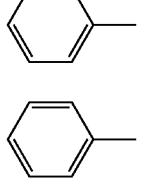 |
TABLE 17
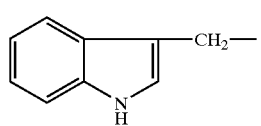
| Compound No. | R² | R⁶ |
|---|---|---|
| E-1 | H | 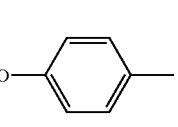 |
| E-2 | H | 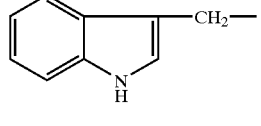 |
| E-3 | H | 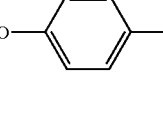 |
TABLE 17-continued
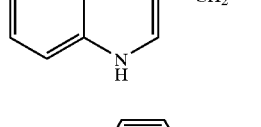
| Compound No. | R² | R⁶ |
|---|---|---|
| E-4 | HOOCCH₂— | 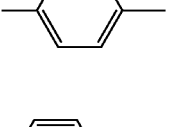 |
| E-5 | 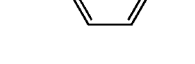 | 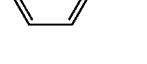 |
| E-6 | 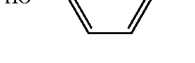 | 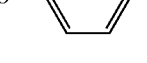 |
| E-7 | 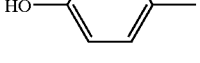 | 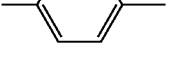 |
| E-8 | 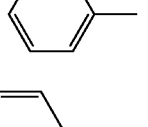 | 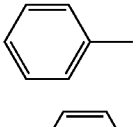 |
| E-9 | 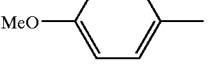 | 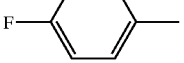 |
| E-10 | 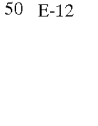 |  |
| E-11 | i-Bu | 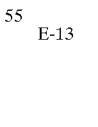 |
| E-12 | i-Pr | 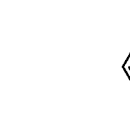 |
| E-13 | Bn |  |
| E-14 | HOOCCH₂— | 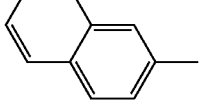 |

TABLE 17-continued

[Structure: R⁶-thiazole-phenyl-SO₂NH-CH(R²)-COOH]

| Compound No. | R² | R⁶ |
|---|---|---|
| E-15 | MeSCH₂CH₂— | 2-naphthyl |
| E-16 | indol-3-ylmethyl (3-CH₂-indole) | 2-naphthyl |

TABLE 18

| Compound No. | R² | R⁶ |
|---|---|---|
| E-17 | 4-HO-C₆H₄-CH₂— | 2-naphthyl |
| E-18 | i-Bu | 2-naphthyl |
| E-19 | H | 2-naphthyl |

TABLE 19

[Structure: R⁶-thiazole-thiophene-SO₂NH-CH(R²)-COOH]

| Compound No. | R² | R⁶ |
|---|---|---|
| F-1 | Me | phenyl |
| F-2 | H | phenyl |
| F-3 | HOOCCH₂— | phenyl |

TABLE 19-continued

| Compound No. | R² | R⁶ |
|---|---|---|
| F-4 | MeSCH₂CH₂— | phenyl |
| F-5 | indol-3-ylmethyl | phenyl |
| F-6 | 4-HO-C₆H₄-CH₂— | phenyl |
| F-7 | i-Bu | phenyl |

Test Example 1

Isolation and Purification of MMP

MMP-1 was purchased from Yagai.

MMP-2 was purchased from Calbiochem-Novabiochem International, Inc.

In regard to MMP-8, catalytic domain ($^{99}$Phe~$^{262}$Gly) was amplified with PCR using commercial available Human Bone Marrow cDNA. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction (Thau F. Ho, M. Walid Qoronfleh, Robert C. Wahl, Trica A. Pulvino, Karen J. Vavra, Joe Falvo, Tracey M. Banks, Patricia G. Brake and Richard B. Ciccarelli: Gene expression, purification and characterization of recombinant human neutrophil collagenase. Gene 146, (1994) 297–301, Prepared by the a improved method of this material). Isolation of MMP-8 from an insoluble fraction was carried out by dissolving in modifier (6M urea) by a usual method and purification with metal chelate chromatography. And then removing modifier (6M urea) with dialysis and refolding of the enzyme spontaneously gave activated MMP-8.

MMP-9 was isolated and purified by procedures described in as follows: Yasunori Okada, Yukio Gonoji, Katsumi Naka, Katsuro Tomita, Isao Nakanishi, Kazushi Iwata, Kyoko Yamashita, and Taro Hayakawa: Matrix metalloproteinase 9 (92-kDa gelatinase/type IV collagenase) from HT1080 human fibrosarcoma cells. Purification and activation of the precursor and enzymic properties J. Biol. Chem., 1992, 267 21712–21719, in combination with others: 1)Yasunori Okada, Tatsuhisa Morodomi, Jan J, Enghild, ko Suzuki, Atsushi Yasui, Isao Nakanishi, Guy Salvesen and Hideaki Nagase: Matrix metalloproteinase 2 from human rheumatoid synovial fibroblasts. Purification and activation of the precursor and enzymic properties. Eur. J. Biochem. 1990, 194

721–730; 2)Robin V Ward, Rosalind M Hembry, John J Reynolds and Gillian Murphy: The purification of tissue inhibitor of metalloproteinase-2 from its 72 kDa progelatinase complex. Biochem. J. 1991 278 179–187. In detail, human fibrosarcoma ATCC HT1080 cell line was cultured to confluent in Dulbecco's Modified Medium (DMEM) containing 10% fetal-calf serum at 37° C. for 48 hours. Subsequently, the medium of confluent culture was changed to serum-free DMEM medium. To obtain MMP-9, Phorbol-12-myristate-13-acetate (TPA) must be added to this serum-free DMEM medium at a concentration of 50 ng/ml. The TPA treated medium was centrifuged at 3000 rpm for 15 min and the supernatant was concentrated to 450 ml by a Toyo-Roshi UP-20 apparatus with an ultrafiltration membrane. Then, proMMP-9 in this concentrated solution was purified by using columns of Gelatin-Sepharose and Concanavalin A-Sepharose. The pool containing proMMP-9 was dialyzed, concentrated (Toyo-Roshi UP-20) and applied to columns of Sephacryl S-200 and Green A matrix for the separation from TIMPs. The obtained proMMP-9 fraction was activated by TPCK-Trypsin (Final conc. 3 μg/501 μl React Mix.).

In regard to MMP-12, catalytic domain($^{100}$Phe~$^{263}$Gly) was amplified with RT-PCR from Human Placenta Total RNA. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-12 from an insoluble fraction was carried out by dissolving in modifier (6M urea) by a usual method and purification with metal chelate chromatography (Ni Chelateing Sepharose). And then removing modifier (6M urea) with dialysis and refolding of the enzyme spontaneously gave activated MMP-12.

In regard to MMP-13, mRNA was prepared from carcinoma cell SW1353 derived from human cartilage stimulate by IL-1, TNF and catalytic domain ($^{104}$Tyr~$^{267}$Gly) was amplified with RT-PCR. This was cloned in *Escherichia. coli* expression vector pTrc99AHE inserted with His-tag sequence and enterokinase digestion-site, induced and expressed by IPTG (Isopropyl-β-D-thiogalactopyranoside) and expressed in a insoluble fraction. Isolation of MMP-13 from an insoluble fraction was carried out by dissolving in modifier (6M urea) by a usual method and purification with metal chelate chromatography (Ni Chelateing Sepharose). And then removing modifier (6M urea) with dialyze and refolding of the enzyme spontaneously gave activated MMP-13.

Test Example 2

Assay for Inhibitory Activities on Various Type of MMPs

The enzymatic activity on MMPs was analyzed by the method described in "C. Graham Knight, Frances Willenbrock and Gillian Murphy: A novel coumarin-labelled peptide for sensitive continuous assays of the matrix metalloproteinases: FEBS LETT., 296, (1992), 263–266". The substrate MOCAc-Pro-Leu-Gly-Leu-A$_2$Pr(DNP)-Ala-Arg-NH$_2$ was purchased from Peptide Institute, Inc., Osaka, Japan. The measurement of the inhibitory activities (IC$_{50}$) was carried out by the following four methods;

(A) Reaction with substrate, enzyme (MMPs) and inhibitor (B) Reaction with substrate and inhibitor, without enzyme (C) Reaction with substrate and enzyme (MMPs), without inhibitor (D) Reaction with substrate only IC$_{50}$ values were calculated by using the following formula and each fluorescence values of above four methods (A to D).

$$\% \text{ inhibition} = \{1-(A-B)/(C-D)\} \times 100$$

IC$_{50}$ means the concentration required to inhibit 50% of the enzyme activity.

The results are shown in Table 20 and Table 21.

TABLE 20

| Compound No. | MMP Inhibitory Activities IC$_{50}$ (nM) | | | | |
|---|---|---|---|---|---|
| | MMP-2 | MMP-8 | MMP-9 | MMP-12 | MMP-13 |
| A-1 | 9.31 | 230 | 212 | 1.88 | 15.0 |
| A-5 | ND | ND | ND | 28.4 | ND |
| A-6 | 9.71 | 233 | 368 | 12.5 | 234 |
| A-8 | 3.37 | 25.2 | 218 | 2.78 | 22.6 |
| A-9 | 287 | 266 | 9320 | 27.3 | 433 |
| A-10 | 5.46 | 97.4 | 135 | 2.42 | 59.2 |
| A-14 | 2.66 | 7.07 | 174 | 1.88 | 5.51 |
| A-16 | 265 | ND | 758 | 26.2 | 774 |
| A-19 | 14.4 | 113 | 247 | 7.71 | 113 |
| A-22 | 7.84 | 53.3 | 144 | 2.69 | 5.31 |
| A-24 | 670 | 337 | 2370 | 10.0 | 678 |
| A-25 | 12.2 | 75.9 | 179 | 7.48 | 140 |
| A-26 | 514 | 569 | 1807 | 40.2 | ND |
| A-27 | 6.08 | 57.3 | 67.9 | 1.55 | 54.5 |
| A-28 | 10.9 | 26.1 | 483 | 5.05 | 44.8 |
| A-30 | 44.4 | 320 | 502 | 11.4 | 226 |
| A-36 | 16.3 | 127 | 226 | 2.98 | 140 |
| A-46 | 7.16 | 279 | 157 | 2.25 | 19.0 |
| A-50 | 4.86 | 146 | 88.6 | 0.699 | 11.9 |
| B-1 | 1.29 | 28.2 | 43.8 | 3.55 | 2.96 |
| B-2 | 1.83 | 15.1 | 13.8 | 2.92 | 14.5 |
| B-3 | 7.45 | 18.9 | 70.5 | 3.16 | 15.0 |
| B-4 | 1.27 | 56.9 | 5.71 | 3.06 | 5.51 |
| B-5 | 5.24 | 25.7 | 14.8 | 1.33 | 6.18 |
| B-6 | 0.347 | 6.47 | 10.0 | 0.370 | 1.16 |
| B-8 | 1.38 | 10.5 | 11.1 | 1.96 | 9.53 |
| B-9 | 8.05 | 12.5 | 55.0 | 1.33 | 13.1 |
| B-10 | 0.373 | 31.7 | 3.96 | 0.643 | 3.38 |
| B-11 | 1.08 | 26.1 | 16.2 | 2.40 | 6.34 |
| B-12 | 1.44 | 25.9 | 66.9 | 3.69 | 9.30 |

TABLE 21

| Compound No. | MMP Inhibitory Activities IC$_{50}$ (nM) | | | | |
|---|---|---|---|---|---|
| | MMP-2 | MMP-8 | MMP-9 | MMP-12 | MMP-13 |
| B-13 | 1.20 | 92.3 | 11.8 | 1.41 | 5.08 |
| B-14 | 2.56 | 72.8 | 19.5 | 2.49 | 11.0 |
| B-17 | 2.09 | 22.4 | 22.6 | 3.21 | 12.1 |
| B-21 | 1.47 | 58.2 | 19.9 | 5.86 | 22.0 |
| B-23 | 0.479 | 15.4 | 16.2 | 1.37 | 2.04 |
| B-24 | 6.30 | 18.5 | 109 | 1.50 | 8.40 |
| B-25 | 0.484 | 51.7 | 5.69 | 0.949 | 4.82 |
| B-26 | 8.30 | 42.5 | 54.4 | 1.24 | 14.1 |
| B-27 | 0.901 | 25.2 | 13.3 | 3.29 | 15.3 |
| B-29 | 0.313 | 45.2 | 5.82 | 0.470 | 2.60 |
| B-31 | 3.57 | 144 | 35.7 | 4.55 | 32.6 |
| B-34 | 1.63 | 24.9 | 53.6 | 3.35 | 6.82 |
| B-38 | 2.14 | 104 | 11.6 | 2.54 | 7.43 |
| B-45 | 2.15 | 29.0 | 26.3 | 2.66 | 17.5 |

TABLE 21-continued

| Compound | MMP Inhibitory Activities IC$_{50}$ (nM) | | | | |
|---|---|---|---|---|---|
| No. | MMP-2 | MMP-8 | MMP-9 | MMP-12 | MMP-13 |
| B-46 | 1.17 | 57.0 | 24.0 | 1.08 | 11.0 |
| B-51 | 0.276 | 66.0 | 4.24 | 0.761 | 2.66 |
| B-52 | 2.50 | 453 | 34.7 | 5.55 | 29.5 |
| B-53 | 2.41 | 373 | 173 | 2.54 | 12.4 |

ND: Not Determined

Compounds including the present invention have broad inhibitory activities against various kinds of MMPs

FORMULATION EXAMPLE

Formulation Example 1

Granules are prepared using the following ingredients.

| Ingredients | |
|---|---|
| The compound represented by the formula (I) | 10 mg |
| Lactose | 700 mg |
| Corn starch | 274 mg |
| HPC-L | 16 mg |
| | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | |
|---|---|
| The compound represented by the formula (I) | 10 mg |
| Lactose | 79 mg |
| Corn starch | 10 mg |
| Magnesium stearate | 1 mg |
| | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | |
|---|---|
| The compound represented by the formula (I) | 15 mg |
| Lactose | 90 mg |
| Corn starch | 42 mg |
| HPC-L | 3 mg |
| | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

Formulation 4

Tablets are prepared using the following ingredients.

| Ingredients | |
|---|---|
| The compound represented by the formula (I) | 10 mg |
| Lactose | 90 mg |
| Microcrystal cellulose | 30 mg |
| CMC-Na | 15 mg |
| Magnesium stearate | 5 mg |
| | 150 mg |

The compound represented by the formula (I), lactose, microcrystal cellulose, and CMC-Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Industrial Applicability

The sulfonamide derivatives of the present invention have inhibiting activities against the matrix metalloproteinase, especially excellent inhibiting activities against plural MMPs and are useful as the treating or preventing agent of diseases caused by MMP.

What is claimed is:
1. A compound of the formula (I):

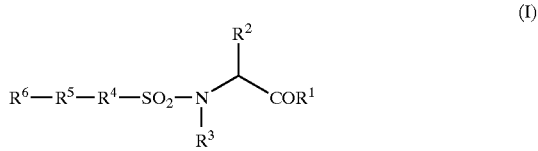

wherein $R^1$ is NHOH, hydroxy, or lower alkyloxy;

$R^2$ is hydrogen atom, optionally substituted lower alkyl, optionally substituted aryl, optionally substituted aralkyl, optionally substituted heteroaryl, or optionally substituted heteroarylalkyl;

$R^3$ is hydrogen atom, optionally substituted lower alkyl, optionally substituted aryl, optionally substituted aralkyl, optionally substituted heteroaryl, or optionally substituted heteroarylalkyl;

$R^4$ is optionally substituted arylene, or optionally substituted heteroarylene;

$R^5$ is:

[chemical structures: oxazole or thiazole]

$R^6$ is optionally substituted aryl, optionally substituted heteroaryl or optionally substituted non-aromatic heterocyclic group; provided that $R^5$ is thiazole-2,5-diyl when $R^4$ is thiophene-2,5-diyl and $R^6$ is optionally substituted phenyl; or an optically active isomer, prodrug, pharmaceutically acceptable salt, or solvate thereof.

2. A compound as claimed in claim 1, wherein $R^6$ is:

[chemical structures]

wherein each $R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, or optionally substituted amino;

m is 0, 1, 2, or 3, an optically active isomer, prodrug, pharmaceutically acceptable salt, or solvate thereof.

3. The compound of claim 1, wherein $R^1$ is hydroxy; or an optically active isomer, prodrug, pharmaceutically acceptable salt, or solvate thereof.

4. The compound of claim 1, wherein $R^2$ is lower alkyl optionally substituted with carboxy, carbamoyl or lower alkylthio, aryl optionally substituted with hydroxy, aralkyl optionally substituted with hydroxy, or heteroarylalkyl optionally substituted with hydroxy, or hydrogen atom; or an optically active isomer, prodrug, pharmaceutically acceptable salt, or solvate thereof.

5. The compound of claim 4, wherein $R^2$ is hydrogen atom, methyl, isopropyl, isobutyl, benzyl, indol-3-ylmethyl, carboxymethyl, 2-methylthioethyl, 4-hydroxybenzyl, or (5-hydroxy-indol-3-yl)methyl; or an optically active isomer, prodrug, pharmaceutically acceptable salt, or solvate thereof.

6. The compound of claim 1, wherein $R^3$ is hydrogen atom; or an optically active isomer, prodrug, pharmaceutically acceptable salt, or solvate thereof.

7. The compound of claim 1, wherein $R^4$ is 1,4-phenylene or 2,5-thiophene-diyl; or an optically active isomer, prodrug, pharmaceutically acceptable salt, or solvate thereof.

8. The compound of claim 2, wherein $R^6$ is:

[chemical structures]

wherein each $R^7$ is each independently hydrogen atom, halogen, lower alkyl, cycloalkyl, lower alkenyl, lower alkynyl, lower alkyloxy, lower alkenyloxy, lower alkylthio, halo(lower)alkyl, hydroxy, carboxy, lower alkyloxycarbonyl, carbamoyl, acyl, nitro, cyano, or optionally substituted amino;

m is 0, 1, 2, or 3; or an optically active isomer, prodrug, pharmaceutically acceptable salt, or solvate thereof.

9. The compound of claim 8, wherein $R^6$ is:

[chemical structure: $R^7$-phenyl]

an optically active isomer, prodrug, pharmaceutically acceptable salt, or solvate thereof.

10. A compound of the formula (II):

[chemical structure of formula (II)]

(II)

wherein $R^8$ is hydrogen atom, methyl, isopropyl, isobutyl, carboxymethyl, carboxyethyl, 2-methylthioethyl, benzyl, 4-hydroxybenzyl, or indol-3-ylmethyl;

$R^9$ is:

[chemical structures: oxazole or thiazole]

$R^{10}$ is hydrogen atom, halogen, lower alkyl, lower alkyloxy, halo(lower)alkyl, acyl, nitro, cyano, optionally substituted amino, or hydroxy; or an optically active isomer, prodrug, pharmaceutically acceptable salt, or solvate thereof.

11. A compound of the formula (III):

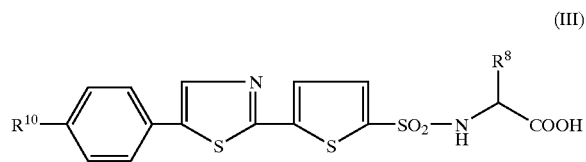

(III)

wherein $R^8$ is hydrogen atom, methyl, isopropyl, isobutyl, carboxymethyl, arboxyethyl, 2-methylthioethyl, benzyl, 4-hydroxybenzyl, or indol-3-ylmethyl;

$R^{10}$ is hydrogen atom, halogen, lower alkyl, lower alkyloxy, halo(lower)alkyl, acyl, nitro, cyano, optionally substituted amino, or hydroxy; or an optically active isomer, prodrug, pharmaceutically acceptable salt, or solvate thereof.

12. A pharmaceutical composition comprising a compound of claim 1, or a optically active isomer, prodrug, pharmaceutically acceptable salt, or solvate thereof, and a pharmaceutically acceptable carrier or excipient.

13. A pharmaceutical composition for inhibiting metalloproteinase comprising a compound of claim 1, or a optically active isomer, prodrug, pharmaceutically acceptable salt, or solvate thereof, and a pharmaceutically acceptable carrier or excipient.

14. A pharmaceutical composition for inhibiting matrix metalloproteinase comprising a compound of claim 1, or a optically active isomer, prodrug, pharmaceutically acceptable salt, or solvate thereof, and a pharmaceutically acceptable carrier or excipient.

15. A method for inhibiting metalloproteinase to treat a disease selected from the group consisting of nephritis, osteoarthritis, heart failure and chronic pulmonary disease, which comprises administering to a mammal a pharmaceutically effective amount of a compound of claim 1, or an optically active isomer, prodrug, pharmaceutically acceptable salt, or solvate thereof.

16. The method of claim 15, wherein said mammal is a human.

* * * * *